(12) United States Patent
Shimizu et al.

(10) Patent No.: US 8,263,622 B2
(45) Date of Patent: Sep. 11, 2012

(54) FUSED-RING DERIVATIVE AND MEDICAL APPLICATION OF SAME

(75) Inventors: Kazuo Shimizu, Azumino (JP); Masato Iizuka, Azumino (JP); Hideki Fujikura, Azumino (JP); Yasushi Takigawa, Azumino (JP); Masahiro Hiratochi, Azumino (JP)

(73) Assignee: Kissei Pharmaceutical Co., Ltd., Matsumoto-shi (JP)

( * ) Notice: Subject to any disclaimer, the term of this patent is extended or adjusted under 35 U.S.C. 154(b) by 0 days.

(21) Appl. No.: 13/124,345

(22) PCT Filed: Oct. 14, 2009

(86) PCT No.: PCT/JP2009/067752
§ 371 (c)(1),
(2), (4) Date: Apr. 14, 2011

(87) PCT Pub. No.: WO2010/044405
PCT Pub. Date: Apr. 22, 2010

(65) Prior Publication Data
US 2011/0207935 A1    Aug. 25, 2011

(30) Foreign Application Priority Data
Oct. 15, 2008   (JP) ................................ 2008-266088

(51) Int. Cl.
| | |
|---|---|
| *A61K 31/426* | (2006.01) |
| *A61K 31/433* | (2006.01) |
| *A61K 31/4709* | (2006.01) |
| *A61K 31/4725* | (2006.01) |
| *C07D 215/16* | (2006.01) |
| *C07D 239/72* | (2006.01) |
| *C07D 277/24* | (2006.01) |

(52) U.S. Cl. ..................... 514/311; 514/266.1; 514/314; 544/283; 546/152; 548/146

(58) Field of Classification Search .................. 548/146; 544/283; 546/152; 514/266.1, 311, 314
See application file for complete search history.

(56) References Cited

U.S. PATENT DOCUMENTS
2003/0073724 A1    4/2003  Shao et al.
2010/0204234 A1    8/2010  Hartmann et al.

FOREIGN PATENT DOCUMENTS
| | | |
|---|---|---|
| EP | 0 569 013 A1 | 11/1993 |
| EP | 0569013 A1 * | 11/1993 |
| JP | 2000-001431 A | 1/2000 |
| WO | 95/33754 A1 | 12/1995 |
| WO | 03/022285 A1 | 3/2003 |
| WO | 2008/116920 A2 | 10/2008 |

OTHER PUBLICATIONS

International Search Report of PCT/JP2009/067752, date of mailing Dec. 22, 2009.

* cited by examiner

*Primary Examiner* — Kamal Saeed
*Assistant Examiner* — Janet L Coppins
(74) *Attorney, Agent, or Firm* — Westerman, Hattori, Daniels & Adrian, LLP

(57) ABSTRACT

The present invention provides compounds useful as agents for the prevention or treatment of a disease associated with abnormal plasma uric acid level and the like. The present invention relates to fused ring derivatives represented by the following formula (I) having xanthine oxidase inhibitory activities and useful as agents for the prevention or treatment of a disease associated with abnormality of plasma uric acid level, prodrugs thereof, salts thereof or the like. In the formula (I), $X^1$ and $X^2$ represent CH or N; ring U represents aryl or heteroaryl; m represents integral number from 0 to 2; n represents integral number from 0 to 3; $R^1$ represents a hydroxy group, amino or $C_{1-6}$ alkyl; $R^2$ represents $C_{1-6}$ alkyl, $C_{1-6}$ alkoxy $C_{1-6}$ alkyl or the like.

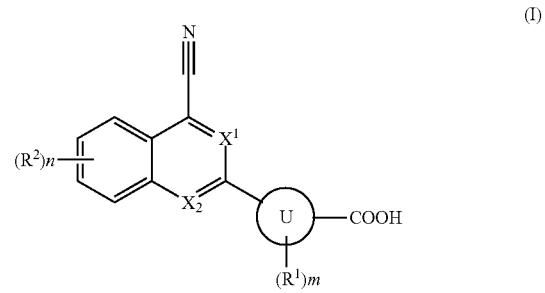

27 Claims, No Drawings

FUSED-RING DERIVATIVE AND MEDICAL APPLICATION OF SAME

TECHNICAL FIELD

The present invention relates to fused ring derivatives useful as medicaments.

More particularly, the present invention relates to fused ring derivatives having xanthine oxidase inhibitory activities and useful as agents for the prevention or treatment of a disease associated with abnormality of serum uric acid level, or prodrugs thereof, or pharmaceutically acceptable salts thereof.

BACKGROUND ART

Uric acid is the final product of purine metabolism in human. In many mammals, unlike human, uric acid is further broken down by urate oxidase (uricase) in the liver into allantoin, which is excreted through the kidney. In human, main pathway of uric acid excretion is the kidney, wherein approximately two thirds of uric acid is excreted in urine. The remaining is excreted in feces. When an excessive production or decreased excretion of uric acid occurs, that causes hyperuricemia. Hyperuricemia is classified into a uric acid overproduction type, a uric acid underexcretion type and a mixed type thereof. This classification of hyperuricemia is clinically important. Aiming for reducing adverse effects of therapeutic agents, therapeutic agents are chosen according to each class (for example, see Non-patent reference 1).

In hyperuricemia with a uric acid overproduction type, urinary excretion of uric acid increases, and when the urinary excretion of uric acid further increases by using of a uricosuric drug, the complication of urinary calculi is possibly developed. Therefore, in principle, allopurinol, a uric acid production inhibitor (or sometimes called a uric acid synthesis inhibitor, hereinafter referred to as "a uric acid production inhibitor"), is used in a uric acid overproduction type.

Uric acid is produced from purine bodies, which are derived from diet and synthesized endogenously, finally by oxidizing xanthine by xanthine oxidase. Allopurinol is developed as a xanthine oxidase inhibitor and an only uric acid production inhibitor used in medical practice. While allopurinol, however, is reported being effective in hyperuricemia and various diseases caused by the same, severe adverse effects such as poisoning syndrome (hypersensitivity angiitis), Stevens-Johnson syndrome, exfoliative dermatitis, aplastic anemia, liver dysfunction and the like have been also reported (for example, see Non-patent reference 2). As one of the causes, it has been pointed out that allopurinol has a nucleic acid-like structure and inhibits a pathway of pyrimidine metabolism (for example, see Non-patent reference 3).

On the other hand, in hyperuricemia with a uric acid underexcretion type, uric acid excretion decreases. It has been reported that when allopurinol, which is metabolized into oxypurinol to be excreted through the kidney by the same mechanism to uric acid, is used, the excretion of oxypurinol also decreases and that increases the incidence of liver disorders (for example, see Non-patent reference 4). Therefore, in principle, uricosuric drugs such as probenecid, benzbromarone and the like are used in a uric acid underexcretion type. These uricosuric drugs, however, also exert adverse effects such as gastrointestinal disorders, urinary calculi or the like. Particularly, benzbromarone is known as possibly causing fulminant hepatitis in the case of idiosyncratic patients (for example, see Non-patent references 5 and 6).

Thus, it is said that both of the existing uric acid production inhibitor and uricosuric drug have usage restrictions in patients or severe adverse effects. Therefore, the development of an easy-to-use agent for the treatment of hyperuricemia or the like has been desired.

Uric acid is eliminated mainly by the kidney, and the urate dynamics in the kidney has been investigated so far in some experiments using brush-border membrane vesicles (BBMV) prepared from the renal cortex (for example, see Non-patent references 7 and 8). It has been known that in human, uric acid is passed through the kidney glomerulus freely, and there are mechanisms of reabsorption and secretion of uric acid in the proximal tubule (for example, see Non-patent reference 9).

In recent years, the gene (SLC22A12) encoding the human kidney urate transporter has been identified (for example, see Non-patent reference 10). The transporter encoded by this gene (urate transporter 1, hereinafter referred to as "URAT1") is a 12-transmembrane type molecule belonging to OAT family. URAT1 mRNA was specifically expressed in the kidney, and localization of URAT1 in apical side of the proximal tubule was observed on the human kidney tissue section. In an experiment using xenopus oocyte expression system, uptake of uric acid through URAT1 was shown. Furthermore, it was shown that the uptake of uric acid is transported by exchange with organic anions such as lactic acid, pyrazinecarboxylic acid (PZA), nicotinic acid and the like, and the uric acid uptake through URAT1 is inhibited by uricosuric drugs, probenecid and benzbromarone. Thus, as expected by the experiment using membrane vesicles, it was strongly suggested that URAT1 is a urate/anion exchanger. That is, it was shown that URAT1 is a transporter that plays an important role in uric acid reabsorption in the kidney (for example, see Non-patent reference 10).

In addition, the relation between URAT1 and diseases became clear. Idiopathic renal hypouricemia is a disease wherein uric acid excretion is increased due to abnormal urate dynamics in the kidney and the serum uric acid level becomes low. It is known that the disease is often associated with urinary calculi or acute renal failure after exercise. URAT1 was identified as a causative gene of the renal hypouricemia (for example, see Non-patent reference 10). These things also strongly suggest that URAT1 is responsible for controlling the blood uric acid level.

Therefore, a substance having a URAT1 inhibitory activity is useful as an agent for the treatment and prevention of diseases associated with high blood uric acid levels, that is, hyperuricemia, gouty tophus, gouty arthritis, renal disorder associated with hyperuricemia, urinary calculi or the like.

In the treatment of hyperuricemia, it was reported that a combination of allopurinol of a uric acid production inhibitor and an agent having a uricosuric activity lowered the serum uric acid level more strongly than the single use of allopurinol (for example, see Non-patent references 11 and 12). Therefore, when treatment with a single existing agent can not exert effect enough, a higher therapeutic effect can be expected by a combination use of a uric acid production inhibitor and a uricosuric agent. Furthermore, for hyperuricemia with the uric acid underexcretion type, it is considered that since urinary excretion of uric acid can be decreased by lowering blood uric acid level, the risk of urinary calculi caused by the monotherapy with a uricosuric agent can be reduced. In addition, for hyperuricemia with the mixed type, high therapeutic effect is expected. Thus, an agent having both an inhibitory activity of uric acid production and a uricosuric activity is expected to become an extremely useful agent for the prevention or treatment of hyperuricemia or the like.

As a compound having both xanthine oxidase inhibitory activity and URAT1 inhibitory activity, morin, a natural product, is known (see Non-patent reference 13). In addition, as a compound having a uricosuric activity, biaryl or diaryl ether compounds are known (see Patent reference 1).

As a compound wherein a fused ring is bound to an aromatic ring having a carboxy group, for example, a naphthalene derivative having a HIV therapeutic effect (see Patent reference 2), a quinoline derivative having a hypotensive effect (see Patent reference 3) and the like are known. However, these have different structures from a fused ring derivative of the present invention. In addition, in the reference, anything is neither described nor suggested about that a fused ring derivative of the present invention has a xanthine oxidase inhibitory activity and is useful for the prevention or treatment of a disease associated with abnormal serum uric acid level such as gout, hyperuricemia or the like.

Patent reference 1: Japanese Patent Publication No. 2000-001431
Patent reference 2: International Publication No. WO95/33754 pamphlet
Patent reference 3: European Patent Publication No. 0569013 specification
Non-patent reference 1: Atsuo Taniguchi and 1 person, *Modern Physician*, 2004, Vol. 24, No. 8, pp. 1309-1312
Non-patent reference 2: Kazuhide Ogino and 2 persons, *Nihon Rinsho* (Japan Clinical), 2003, Vol. 61, Extra edition 1, pp. 197-201
Non-patent reference 3: Hideki Horiuchi and 6 persons, Life Science, 2000, Vol. 66, No. 21, pp. 2051-2070
Non-patent reference 4: Hisashi Yamanaka and 2 persons, *Konyosankessyo to Tsufu* (Hyperuricemia and gout), issued by Medical Review Co., 1994, Vol. 2, No. 1, pp. 103-111
Non-patent reference 5: Robert A Terkeltaub, N. Engl. J. Med., 2003, Vol. 349, pp. 1647-1655
Non-patent reference 6: Ming-Han H. Lee and 3 persons, Drug. Safety, 2008, Vol. 31, pp. 643-665
Non-patent reference 7: Francoise Roch-Ramel and 2 persons, Am. J. Physiol., 1994, Vol. 266 (Renal Fluid Electrolyte Physiol., Vol. 35), F797-F805
Non-patent reference 8: Francoise Roch-Ramel and 2 persons, J. Pharmacol. Exp. Ther., 1997, Vol. 280, pp. 839-845
Non-patent reference 9: Gim Gee Teng and 2 persons, Drugs, 2006, Vol. 66, pp. 1547-1563
Non-patent reference 10: Atsushi Enomoto and 18 persons, Nature, 2002, Vol. 417, pp. 447-452
Non-patent reference 11: S Takahashi and 5 persons, Ann. Rheum. Dis., 2003, Vol. 62, pp. 572-575
Non-patent reference 12: M. D. Feher and 4 persons, Rheumatology, 2003, Vol. 42, pp. 321-325
Non-patent reference 13: Zhifeng Yu and 2 persons, J. Pharmacol. Exp. Ther., 2006, Vol. 316, pp. 169-175

DISCLOSURE OF THE INVENTION

Problem that the Invention Aims to Solve

The present invention is to provide an agent which has an inhibitory activity of uric acid production for the prevention or treatment of a disease associated with abnormal serum uric acid level.

Means to Solve the Problem

The present inventors have studied earnestly to solve the above problem. As a result, it was found that fused ring derivatives represented by the following formula (I) exert an excellent xanthine oxidase inhibitory activity and extremely lower serum uric acid levels, and therefore, they can be a novel agent for the prevention or treatment of a disease associated with abnormal serum uric acid level, thereby forming the basis of the present invention.

That is, the present invention relates to:
[1] a fused ring derivative represented by the formula (I):

[Chem. 1]

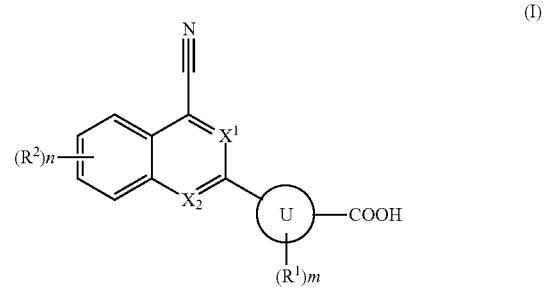

wherein
$X^1$ and $X^2$ independently represent CH or N;
ring U represents $C_6$ aryl or 5 or 6-membered heteroaryl;
m represents an integral number from 0 to 2;
n represents an integral number from 0 to 3;
$R^1$ represents a hydroxy group, a halogen atom, amino or $C_{1-6}$ alkyl, and when m is 2, two $R^1$ are optionally different from each other;
$R^2$ represents any of (1) to (11):
(1) a halogen atom;
(2) a hydroxy group;
(3) cyano;
(4) nitro;
(5) carboxy;
(6) carbamoyl;
(7) amino;
(8) $C_{1-6}$ alkyl, $C_{2-6}$ alkenyl or $C_{1-6}$ alkoxy each of which may independently have any (preferably 1 to 3) group selected from substituent group α;
(9) $C_{2-6}$ alkynyl, $C_{1-6}$ alkylsulfonyl, mono(di)$C_{1-6}$ alkylsulfamoyl, $C_{2-7}$ acyl, $C_{1-6}$ alkoxycarbonyl, $C_{1-6}$ alkoxycarbonyloxy, mono(di)$C_{1-6}$ alkylamino, mono(di)$C_{1-6}$ alkoxy $C_{1-6}$ alkylamino, $C_{1-6}$ alkoxy $C_{1-6}$ alkyl($C_{1-6}$ alkyl)amino, $C_{2-7}$ acylamino, $C_{1-6}$ alkoxycarbonylamino, $C_{1-6}$ alkoxycarbonyl($C_{1-6}$ alkyl)amino, mono(di)$C_{1-6}$ alkylcarbamoyl, mono(di)$C_{1-6}$ alkoxy $C_{1-6}$ alkylcarbamoyl, $C_{1-6}$ alkoxy $C_{1-6}$ alkyl($C_{1-6}$ alkyl)carbamoyl, mono(di)$C_{1-6}$ alkylaminocarbonylamino, $C_{1-6}$ alkylsulfonylamino or $C_{1-6}$ alkylthio each of which may independently have any 1 to 3 groups selected from a fluorine atom, a hydroxy group and amino;
(10) $C_{3-8}$ cycloalkyl, 3 to 8-membered heterocycloalkyl, $C_{5-8}$ cycloalkenyl or 5 to 8-membered heterocycloalkenyl each of which may independently have any 1 to 3 groups selected from a fluorine atom, a hydroxy group, amino, oxo, $C_{1-6}$ alkyl, $C_{1-6}$ alkoxy, $C_{1-6}$ alkoxy $C_{1-6}$ alkyl, carboxy, $C_{2-7}$ acyl, $C_{1-6}$ alkoxycarbonyl, carbamoyl, mono(di)$C_{1-6}$ alkylcarbamoyl, mono(di)$C_{1-6}$ alkoxy $C_{1-6}$ alkylcarbamoyl and $C_{1-6}$ alkoxy $C_{1-6}$ alkyl ($C_{1-6}$ alkyl)carbamoyl;
(11) $C_6$ aryl, $C_6$ aryloxy, $C_6$ arylcarbonyl, 5 or 6-membered heteroaryl, 5 or 6-membered heteroaryloxy, 5 or 6-membered heteroarylcarbonyl, $C_6$ arylamino, $C_6$ aryl($C_{1-6}$ alkyl)amino, 5 or 6-membered heteroarylamino or 5 or 6-membered heteroaryl($C_{1-6}$ alkyl)amino each of which may independently have any 1 to 3 groups selected from a halogen atom, a hydroxy group, amino, cyano, nitro, $C_{1-6}$ alkyl, $C_{1-6}$ alkoxy, $C_{1-6}$ alkoxy $C_{1-6}$ alkyl, carboxy, $C_{2-7}$ acyl, $C_{1-6}$ alkoxycarbonyl, carbamoyl, mono(di) $C_{1-6}$ alkylcarbamoyl, mono(di($C_{1-6}$ alkylamino, mono (di($C_{1-6}$ alkoxy $C_{1-6}$ alkylamino, $C_{1-6}$ alkoxy $C_{1-6}$ alkyl ($C_{1-6}$ alkyl)amino, $C_{1-6}$ alkoxycarbonylamino, mono(di ($C_{1-6}$ alkoxy $C_{1-6}$ alkylcarbamoyl and $C_{1-6}$ alkoxy $C_{1-6}$ alkyl($C_{1-6}$ alkyl)carbamoyl; and when n is 2 or 3, these $R^2$ are optionally different from each other, and when two $R^2$ bound to the neighboring atoms exist and independently represent $C_{1-6}$ alkyl or $C_{1-6}$ alkoxy each of which may have $C_{1-6}$ alkoxy, these two $R^2$ optionally form a 5 to 8-membered ring together with the binding atoms;

substituent group a consists of a fluorine atom; a hydroxy group; amino; carboxy; $C_{1-6}$ alkoxy, mono(di)$C_{1-6}$ alkylamino, mono(di)$C_{1-6}$ alkoxy $C_{1-6}$ alkylamino, $C_{1-6}$ alkoxy $C_{1-6}$ alkyl($C_{1-6}$ alkyl)amino, $C_{1-6}$ alkoxycarbonylamino, $C_{2-7}$ acyl, $C_{1-6}$ alkoxycarbonyl, mono(di)$C_{1-6}$ alkylcarbamoyl, mono(di)$C_{1-6}$ alkoxy $C_{1-6}$ alkylcarbamoyl, $C_{1-6}$ alkoxy $C_{1-6}$ alkyl($C_{1-6}$ alkyl)carbamoyl, $C_{1-6}$ alkylsulfonylamino, $C_{2-7}$ acylamino and $C_{1-6}$ alkoxycarbonylamino each of which may have any 1 to 3 groups selected from a fluorine atom, a hydroxy group and amino; $C_{3-8}$ cycloalkyl and 3 to 8-membered heterocycloalkyl each of which may independently have any 1 to 3 groups selected from a fluorine atom, a hydroxy group, amino, oxo, $C_{1-6}$ alkyl, $C_{1-6}$ alkoxy, $C_{1-6}$ alkoxy $C_{1-6}$ alkyl, carboxy, $C_{2-7}$ acyl, $C_{1-6}$ alkoxycarbonyl, carbamoyl, mono(di($C_{1-6}$ alkylcarbamoyl, mono(di($C_{1-6}$ alkoxy $C_{1-6}$ alkylcarbamoyl and $C_{1-6}$ alkoxy $C_{1-6}$ alkyl($C_{1-6}$ alkyl)carbamoyl; and $C_6$ aryl and 5 or 6-membered heteroaryl each of which may independently have any 1 to 3 groups selected from a halogen atom, a hydroxy group, amino, cyano, nitro, $C_{1-6}$ alkyl, $C_{1-6}$ alkoxy, $C_{1-6}$ alkoxy $C_{1-6}$ alkyl, carboxy, $C_{2-7}$ acyl, $C_{1-6}$ alkoxycarbonyl, carbamoyl, mono(di ($C_{1-6}$ alkylcarbamoyl, mono(di($C_{1-6}$ alkylamino, mono(di ($C_{1-6}$ alkoxy $C_{1-6}$ alkylamino, $C_{1-6}$ alkoxy $C_{1-6}$ alkyl($C_{1-6}$ alkyl)amino, $C_{1-6}$ alkoxycarbonylamino, mono(di($C_{1-6}$ alkoxy $C_{1-6}$ alkylcarbamoyl and $C_{1-6}$ alkoxy $C_{1-6}$ alkyl($C_{1-6}$ alkyl)carbamoyl, or a prodrug thereof, or a pharmaceutically acceptable salt thereof;

[2] a fused ring derivative as described in the above [1], wherein $X^1$ represents CH, or a prodrug thereof, or a pharmaceutically acceptable salt thereof;

[3] a fused ring derivative as described in the above [1] or [2], wherein $X^2$ represents CH, or a prodrug thereof, or a pharmaceutically acceptable salt thereof;

[4] a fused ring derivative as described in any one of the above [1] to [3], wherein ring U represents a benzene ring, a pyridine ring, a thiazole ring, a pyrazole ring or a thiophene ring, or a prodrug thereof, or a pharmaceutically acceptable salt thereof;

[5] a fused ring derivative as described in the above [4], wherein m is 0, or m is 1 and ring U is any one of rings represented by the following formula:

[Chem. 2]

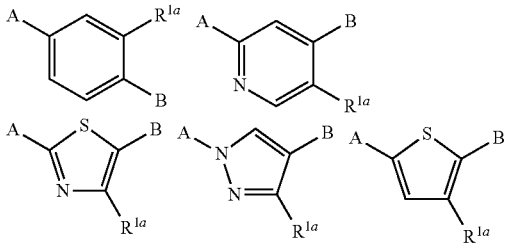

in the formula, $R^{1a}$ represents a hydroxy group, amino or $C_{1-6}$ alkyl; A represents a bond with the fused ring; and B represents a bond with carboxy; respectively, or a prodrug thereof, or a pharmaceutically acceptable salt thereof;

[6] a fused ring derivative as described in the above [5], wherein ring U represents a thiazole ring, or a prodrug thereof, or a pharmaceutically acceptable salt thereof;

[7] a fused ring derivative as described in the above [5], wherein ring U represents a pyridine ring, or a prodrug thereof, or a pharmaceutically acceptable salt thereof;

[8] a fused ring derivative as described in the above [6], wherein $R^{1a}$ represents a methyl group; n is 0, or n is 1 to 3 and $R^2$ represents a halogen atom, a hydroxy group or $C_{1-6}$ alkyl which may have 1 to 3 fluorine atoms, or a prodrug thereof, or a pharmaceutically acceptable salt thereof;

[9] a fused ring derivative as described in the above [7], wherein m is 0; or m is 1, $R^{1a}$ represents a hydroxy group and $R^2$ represents a halogen atom, a hydroxy group or $C_{1-6}$ alkyl which may have 1 to 3 fluorine atoms, or a prodrug thereof, or a pharmaceutically acceptable salt thereof;

[10] a fused ring derivative as described in any one of the above [1] to [7], wherein n is 0, or n is 1 to 3 and $R^2$ represents a halogen atom, a hydroxy group, or $C_{1-6}$ alkyl or $C_{1-6}$ alkoxy each of which may independently have any 1 to 3 groups selected from a fluorine atom, a hydroxy group and amino, or a prodrug thereof, or a pharmaceutically acceptable salt thereof;

[11] a fused ring derivative as described in the above [10], wherein n is 0, or n is 1 to 3 and $R^2$ represents a halogen atom, or $C_{1-6}$ alkyl or $C_{1-6}$ alkoxy each of which may independently have any 1 to 3 groups selected from a fluorine atom, a hydroxy group and amino; and ring U represents a thiazole ring or a pyridine ring, or a prodrug thereof, or a pharmaceutically acceptable salt thereof;

[12] a fused ring derivative as described in any one of the above [1] to [11], wherein m is 0, or a prodrug thereof, or a pharmaceutically acceptable salt thereof;

[13] a fused ring derivative as described in any one of the above [1] to [12], wherein n is 0, or a prodrug thereof, or a pharmaceutically acceptable salt thereof;

[14] a fused ring derivative as described in the above [10], wherein n is 1 to 3; and $R^2$ represents a fluorine atom, or a prodrug thereof, or a pharmaceutically acceptable salt thereof;

[15] a fused ring derivative as described in the above [11], represented by the formula (Ib):

[Chem. 3]

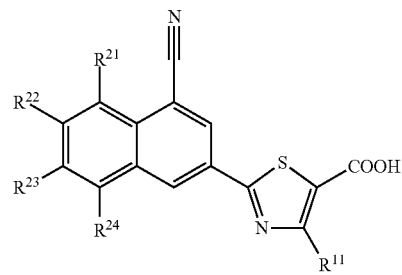

(Ib)

wherein $R^{21}$ represents a hydrogen atom, a fluorine atom or a methyl group; $R^{22}$ represents a hydrogen atom or a fluorine atom; $R^{23}$ represents a hydrogen atom, a fluorine atom or a methyl group; $R^{24}$ represents a hydrogen atom or a fluorine atom; and $R^{11}$ represents a hydrogen atom or a methyl group, or a prodrug thereof, or a pharmaceutically acceptable salt thereof;

[16] a fused ring derivative as described in any one of the above [1] to [15], which is a xanthine oxidase inhibitor, or a prodrug thereof, or a pharmaceutically acceptable salt thereof;

[17] a pharmaceutical composition comprising as an active ingredient a fused ring derivative as described in any one of the above [1] to [15], or a prodrug thereof, or a pharmaceutically acceptable salt thereof;

[18] a pharmaceutical composition as described in the above [17], which is an agent for the prevention or treatment of a disease selected from the group consisting of hyperuricemia, gouty tophus, gouty arthritis, renal disorder associated with hyperuricemia and urinary calculi;

[19] a pharmaceutical composition as described in the above [18], which is an agent for the prevention or treatment of hyperuricemia;

[20] a pharmaceutical composition as described in the above [17], which is an agent for lowering plasma uric acid level;

[21] a pharmaceutical composition as described in the above [17], which is a uric acid production inhibitor; and the like.

In the present invention, each term has the following meaning unless otherwise specified.

The term "halogen atom" means a fluorine atom, a chlorine atom, a bromine atom or an iodine atom.

The term "$C_{1-6}$ alkyl" means a straight-chained or a branched alkyl group having 1 to 6 carbon atoms, and for example, methyl, ethyl, propyl, isopropyl, butyl, isobutyl, sec-butyl, tert-butyl and the like can be illustrated.

The term "$C_{1-6}$ alkylene" means a divalent group derived from the above $C_{1-6}$ alkyl.

The term "$C_{2-6}$ alkenyl" means a straight-chained or a branched alkenyl group having 2 to 6 carbon atoms, and vinyl, allyl, 1-propenyl, isopropenyl and the like can be illustrated.

The term "$C_{2-6}$ alkynyl" means a straight-chained or a branched alkynyl group having 2 to 6 carbon atoms, and ethynyl, 2-propynyl and the like can be illustrated.

The term "$C_{1-6}$ alkoxy" means a straight-chained or a branched alkoxy group having 1 to 6 carbon atoms, and methoxy, ethoxy, propoxy, isopropoxy and the like can be illustrated.

The term "$C_{1-6}$ alkoxycarbonyl" means a group represented by ($C_{1-6}$ alkoxy)-C(O)—, and methoxycarbonyl, ethoxycarbonyl, propoxycarbonyl, isopropoxycarbonyl and the like can be illustrated.

The term "$C_{1-6}$ alkoxycarbonyloxy" means a group represented by ($C_{1-6}$ alkoxy)-C(O)O—.

The term "$C_{1-6}$ alkoxy $C_{1-6}$ alkyl" means the above $C_{1-6}$ alkyl substituted by the above $C_{1-6}$ alkoxy.

The term "$C_{1-6}$ alkylsulfonyl" means a group represented by ($C_{1-6}$ alkyl)-SO$_2$—, and methylsulfonyl, ethylsulfonyl and the like can be illustrated.

The term "$C_{1-6}$ alkylsulfonylamino" means a group represented by ($C_{1-6}$ alkyl)-SO$_2$NH—, and methylsulfonylamino, ethylsulfonylamino and the like can be illustrated.

The term "mono(di)$C_{1-6}$ alkylsulfamoyl" means a sulfamoyl group mono- or di-substituted by the above $C_{1-6}$ alkyl.

The term "$C_{2-7}$ acyl" means a group represented by ($C_{1-6}$ alkyl)-C(O)—, and acetyl, propionyl, butyryl, isobutyryl, pivaloyl and the like can be illustrated.

The term "$C_{1-6}$ alkylthio" means a group represented by ($C_{1-6}$ alkyl)-S—.

The term "mono(di)$C_{1-6}$ alkylamino" means an amino group mono- or di-substituted by the above $C_{1-6}$ alkyl, the term "mono(di)$C_{1-6}$ alkoxy $C_{1-6}$ alkylamino" means an amino group mono- or di-substituted by the above $C_{1-6}$ alkoxy $C_{1-6}$ alkyl, and the term "$C_{1-6}$ alkoxy $C_{1-6}$ alkyl($C_{1-6}$ alkyl)amino" means an amino group substituted by the above $C_{1-6}$ alkoxy $C_{1-6}$ alkyl and the above $C_{1-6}$ alkyl.

The term "$C_{2-7}$ acylamino" means a group represented by ($C_{1-6}$ alkyl)-C(O)NH—.

The term "$C_{1-6}$ alkoxycarbonylamino" means an amino group substituted by the above $C_{1-6}$ alkoxycarbonyl, and the term "$C_{1-6}$ alkoxycarbonyl($C_{1-6}$ alkyl)amino" means an amino group substituted by the above $C_{1-6}$ alkoxycarbonyl and the above $C_{1-6}$ alkyl.

The term "mono(di)$C_{1-6}$ alkylaminocarbonylamino" means a group represented by (mono(di)$C_{1-6}$ alkylamino)-C(O)NH—.

The term "mono(di)$C_{1-6}$ alkylcarbamoyl" means a carbamoyl group mono- or di-substituted by the above $C_{1-6}$ alkyl, the term "mono(di)$C_{1-6}$ alkoxy $C_{1-6}$ alkylcarbamoyl" means a carbamoyl group mono- or di-substituted by the above $C_{1-6}$ alkoxy $C_{1-6}$ alkyl and the term "$C_{1-6}$ alkoxy $C_{1-6}$ alkyl($C_{1-6}$ alkyl)carbamoyl" means a carbamoyl group substituted by the above $C_{1-6}$ alkoxy $C_{1-6}$ alkyl and the above $C_{1-6}$ alkyl. These substituents may be different from each other in the case of di-substitution.

The term "$C_{3-8}$ cycloalkyl" means a 3 to 8-membered saturated cyclic hydrocarbon group, and cyclopropyl, cyclobutyl, cyclopentyl, cyclohexyl, cycloheptyl or cyclooctyl can be illustrated.

The term "$C_{5-8}$ cycloalkenyl" means a 5 to 8-membered cycloalkenyl group, and cyclopropenyl, cyclobutenyl, cyclopentenyl and the like can be illustrated.

The term "3 to 8-membered heterocycloalkyl" means a 3 to 8-membered heterocycloalkyl group having 1 or 2 hetero atoms selected from an oxygen atom, a sulfur atom and a nitrogen atom in the ring, and aziridino, azetidino, morpholino, 2-morpholinyl, thiomorpholino, 1-pyrrolidinyl, piperidino, 4-piperidinyl, 1-piperazinyl, 1-pyrrolyl, tetrahydrofuryl, tetrahydropyranyl and the like can be illustrated.

The term "5 to 8-membered heterocycloalkenyl" means a 5 to 8-membered heterocycloalkenyl group having any 1 or 2 hetero atoms selected from an oxygen atom, a sulfur atom and a nitrogen atom in the ring, and 2,3-dihydrofuryl, 2,5-dihydrofuryl, 3,4-dihydro-2H-pyran and the like can be illustrated.

The term "$C_6$ aryl" means phenyl.

The term "$C_6$ aryloxy" means a group represented by ($C_6$ aryl)-O—, and phenyloxy and the like can be illustrated.

The term "$C_6$ arylcarbonyl" means a group represented by ($C_6$ aryl)-C(O)—, and benzoyl and the like can be illustrated.

The term "$C_6$ arylamino" means a group represented by ($C_6$ aryl)-NH—.

The term "$C_6$ aryl($C_{1-6}$ alkyl)amino" means an amino group substituted by the above $C_6$ aryl and the above $C_{1-6}$ alkyl.

The term "5 or 6-membered heteroaryl" means a 5 or 6-membered aromatic heterocyclic group having any 1 to 4 hetero atoms selected from an oxygen atom, a sulfur atom and a nitrogen atom in the ring, and thiazolyl, oxazolyl, isothiazolyl, isoxazolyl, pyridyl, pyrimidyl, pyrazinyl, pyridazinyl, pyrrolyl, furyl, thienyl, imidazolyl, pyrazoyl, oxadiazolyl, thiadiazolyl, triazolyl, tetrazolyl, furazanyl and the like can be illustrated.

The term "5 or 6-membered heteroaryloxy" means a group represented by (5 or 6-membered heteroaryl)-O—.

The term "5 or 6-membered heteroarylcarbonyl" means a group represented by (5 or 6-membered heteroaryl)-C(O)—.

The term "5 or 6-membered heteroarylamino" means a group represented by (5 or 6-membered heteroaryl)-NH—.

The term "5 or 6-membered heteroaryl($C_{1-6}$ alkyl)amino" means an amino group substituted by the above 5 or 6-membered heteroaryl and the above $C_{1-6}$ alkyl.

A fused ring derivative represented by the formula (I) of the present invention can be prepared, for example, by a method described below or a similar method thereto, or a method described in literatures or a similar method thereto and the like. In addition, when a protective group is necessary, operations of introduction and deprotection can be conducted optionally in combination according to a general method. Each reaction can be also optionally conducted by using a pressure-resistant reaction container.

[Synthetic Method 1]

Among the fused ring derivatives represented by the formula (I) of the present invention, Compound (Ia) wherein $X^1$ and $X^2$ represent CH can be also prepared, for example, by Synthetic method 2.

[Synthetic Method 2]

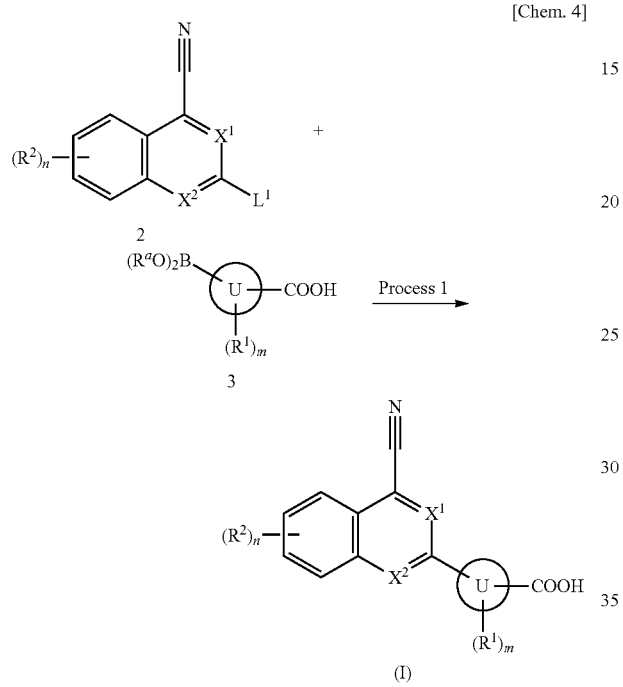

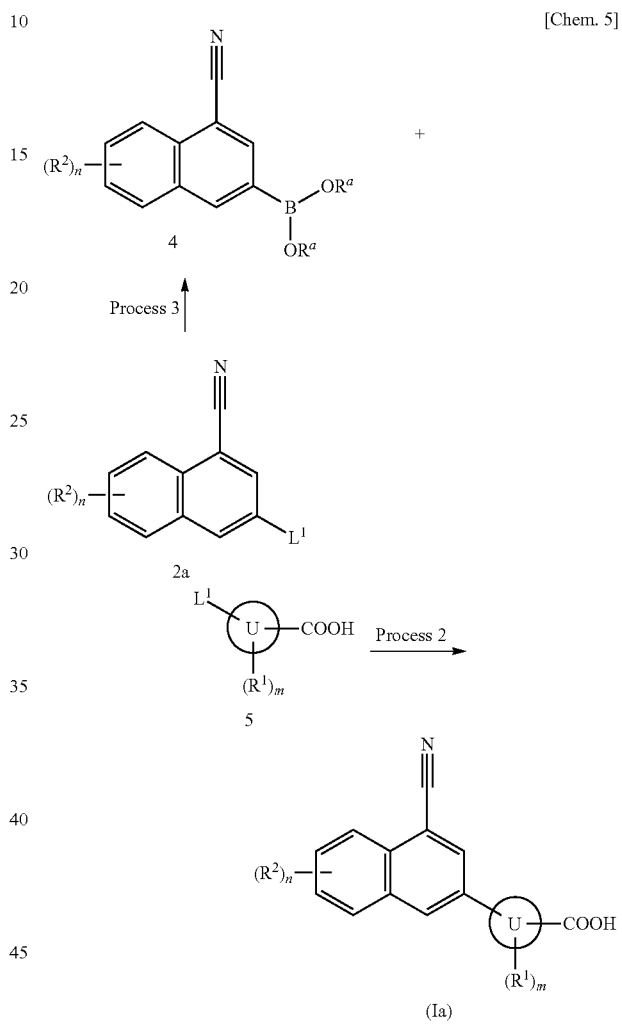

In the formula, $L^1$ represents a leaving group such as a chlorine atom, a bromine atom, an iodine atom, a trifluoromethanesulfonyloxy group or the like, $R^a$ represents a hydrogen atom or $C_{1-6}$ alkyl with the proviso that two $R^a$ may be different or both $R^a$ may bind together to form a ring, and $X^1$, $X^2$, ring U, m, n, $R^1$ and $R^2$ have the same meanings as defined above.

Process 1

A fused ring derivative (I) of the present invention can be also prepared by conducting Suzuki-Miyaura coupling of Compound (2) and Compound (3) in an inert solvent in the presence of a base and a palladium catalyst and optionally removing a protective group. As the inert solvent, benzene, toluene, xylene, diethyl ether, tetrahydrofuran, 1,4-dioxane, 1,2-dimethoxyethane, dichloromethane, 1,2-dichloroethane, chloroform, methanol, ethanol, 2-propanol, butanol, N,N-dimethylformamide, N-methylpyrrolidone, dimethylsulfoxide, water, a mixed solvent thereof and the like can be illustrated. As the base, sodium carbonate, potassium carbonate, cesium carbonate, sodium hydroxide, potassium hydroxide, lithium hydroxide, sodium ethoxide, sodium methoxide, potassium fluoride, cesium fluoride, triethylamine, N,N-diisopropylethylamine, pyridine, 2,6-lutidine, 1,8-diazabicyclo[5,4,0]-7-undecene and the like can be illustrated. As the palladium catalyst, tetrakis(triphenylphosphine)palladium, dichloro-bis(triphenylphosphine)palladium, 1,1'-bis(diphenylphosphino)ferrocene-palladium dichloride and the like can be illustrated. The reaction temperature is usually at 0° C. to reflux temperature, and the reaction time is usually from 30 minutes to 7 days, varying based on a used starting material, solvent and reaction temperature or the like.

In the formula, $L^1$, $R^a$, ring U, m, n, $R^1$ and $R^2$ have the same meanings as defined above.

Process 2

A fused ring derivative (Ia) of the present invention can be also prepared by conducting Suzuki-Miyaura coupling reaction of Compound (4) and Compound (5) by a method similar to that of Process 1 and optionally removing a protective group.

Process 3

Compound (4) used in the above Process 2 can be also prepared by allowing the corresponding Compound (2a) to react with the corresponding boronic acid reagent in an inert solvent in the presence of a base and a palladium catalyst in the presence or absence of a ligand. As the inert solvent, benzene, toluene, xylene, N,N-dimethylformamide, 1,2-dimethoxyethane, 1,4-dioxane, tetrahydrofuran, dimethylsulfoxide, N-methylpyrrolidone, a mixed solvent thereof and the like can be illustrated. As the base, triethylamine, N,N-diisopropylethylamine, pyridine, 2,6-lutidine, sodium carbonate, potassium carbonate, cesium carbonate, potassium acetate, sodium acetate and the like can be illustrated. As the palladium catalyst, palladium acetate, tetrakis(triphenylphosphine)palladium, dichlorobis(triphenylphosphine)palladium, 1,1'-bis(diphenylphosphino)ferrocene-palladium dichloride and the like can be illustrated. As the ligand, bis(diphenylphosphino)ferrocene, tricyclohexylphosphine, 2-(dicyclohexylphosphino)biphenyl and the like can be illustrated. As the boronic acid reagent, pinacolborane, catecholborane, bis(pinacolate)diboron and the like can be illustrated. The reaction temperature is usually at 0° C. to reflux temperature, and the reaction time is usually from 30 minutes to 7 days, varying based on a used starting material, solvent and reaction temperature or the like.

In Process 3, when $L^1$ represents a bromine atom or an iodine atom, Compound (4) can be also prepared by treating Compound (2a) with an organometallic reagent and allowing it to react with a borate ester in an inert solvent. As the inert solvent, diethyl ether, tetrahydrofuran, 1,2-dimethoxyethane, dioxane, benzene, toluene, hexane, a mixed solvent thereof and the like can be illustrated. As the organometallic reagent, isopropylmagnesium bromide, phenylmagnesium bromide, n-butyllithium, sec-butyllithium, tert-butyllithium and the like can be illustrated. As the the boronate ester, trimethyl borate, triethyl borate, triisopropyl borate, tributyl borate, triisopropyl borate, tris(trimethylsilyl)borate and the like can be illustrated. The reaction temperature is usually at −78° C. to reflux temperature, and the reaction time is usually from 30 minutes to 7 days, varying based on a used starting material, solvent and reaction temperature or the like.

Among the compounds represented by Compound (2), Compound (2b) wherein $X^1$ and $X^2$ represent CH, and $L^1$ represents a chlorine atom, a bromine atom or an iodine atom can be also prepared, for example, by Synthetic method 3.
[Synthetic Method 3]

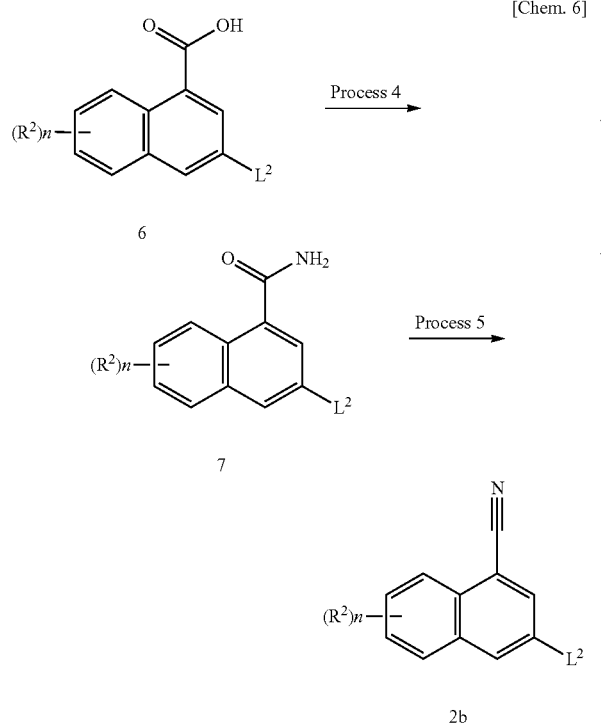

In the formula, $L^2$ represents a chlorine atom, a bromine atom or an iodine atom, n and $R^2$ have the same meanings as defined above.

Process 4
Compound (7) can be prepared by subjecting Compound (6) and ammonia to amidation optionally using an additive agent such as 1-hydroxybenzotriazole or the like in an inert solvent in the presence of a condensation agent in the presence or absence of a base. As the inert solvent, tetrahydrofuran, 1,4-dioxane, 1,2-dimethoxyethane, benzene, toluene, xylene, dichloromethane, 1,2-dichloroethane, chloroform, a mixed solvent thereof and the like can be illustrated. As the condensation agent, acetic anhydride, thionyl chloride, oxalyl chloride, N,N'-carbonyldiimidazole, N,N'-dicyclohexylcarbodiimide, diisopropylcarbodiimide, N-ethyl-N'-3-dimethylaminopropylcarbodiimide and a hydrochloride salt thereof, diphenylphosphorylazide and the like can be illustrated. As the base, triethylamine, N,N-diisopropylethylamine, pyridine, 2,6-lutidine and the like can be illustrated. The reaction temperature is usually at 0° C. to reflux temperature, and the reaction time is usually from 30 minutes to 7 days, varying based on a used starting material, solvent and reaction temperature or the like.

Process 5
Compound (2b) can be prepared by treating Compound (7) in an inert solvent in the presence of a dehydrating agent in the presence or absence of a base. As the inert solvent, tetrahydrofuran, 1,4-dioxane, 1,2-dimethoxyethane, N,N-dimethylformamide, acetonitrile, benzene, toluene, xylene, dichloromethane, 1,2-dichloroethane, chloroform, a mixed solvent thereof and the like can be illustrated. As the dehydrating agent, acetic anhydride, trifluoroacetic anhydride, thionyl chloride, phosphoryl chloride, methanesulfonylimidazole, p-toluenesulfonylchloride, N,N'-dicyclohexylcarbodiimide, diphosphorus pentachloride, triphosgene and the like can be illustrated. As the base, triethylamine, N,N-diisopropylethylamine, pyridine, 2,6-lutidine and the like can be illustrated. The reaction temperature is usually at 0° C. to reflux temperature, and the reaction time is usually from 30 minutes to 7 days, varying based on a used starting material, solvent and reaction temperature or the like.

Also, the above Compound (Ia) of the present invention can be also prepared, for example, by Synthetic method 4.
[Synthetic Method 4]

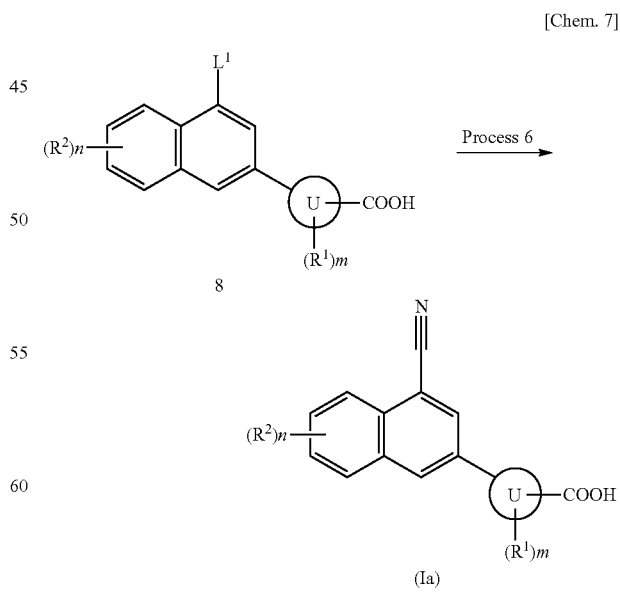

In the formula, $L^1$, ring U, m, n, $R^1$ and $R^2$ have the same meanings as defined above.

Process 6

A fused ring derivative (Ia) of the present invention can be also prepared by allowing Compound (8) to react with a cyanation reagent in an inert solvent in the presence or absence of a base in the presence or absence of a palladium catalyst and optionally removing a protective group. As the inert solvent, benzene, toluene, xylene, diethyl ether, tetrahydrofuran, 1,4-dioxane, 1,2-dimethoxyethane, methanol, ethanol, 2-propanol, butanol, ethylene glycol, N,N-dimethylformamide, N,N-dimethylacetamide, N-methylpyrrolidone, dimethylsulfoxide, hexamethylphosphorylamide, water, a mixed solvent thereof and the like can be illustrated. As the base, sodium carbonate, potassium carbonate, cesium carbonate, sodium hydroxide, potassium hydroxide, lithium hydroxide, sodium ethoxide, sodium methoxide, potassium fluoride, cesium fluoride, triethylamine, N,N-diisopropylethylamine, pyridine, 2,6-lutidine, 1,8-diaza-bicyclo[5,4,0]-7-undecene and the like can be illustrated. As the palladium catalyst, tetrakis(triphenylphosphine)palladium, dichlorobis(triphenylphosphine)palladium, 1,1'-bis(diphenylphosphino)ferrocene-palladium dichloride, palladium acetate, palladium trifluoroacetate and the like can be illustrated. As the cyanation reagent, copper cyanide, sodium cyanide, potassium cyanide, zinc cyanide, trimethylsilyl cyanide, potassium ferrocyanide and the like can be illustrated. The reaction temperature is usually at 0° C. to reflux temperature, and the reaction time is usually from 30 minutes to 7 days, varying based on a used starting material, solvent and reaction temperature or the like.

In Compound (8), Compound (8a) wherein $L^1$ represents a chlorine atom, a bromine atom or an iodine atom, ring U represents a thiazole ring, m is 1, and $R^1$ represents $C_{1-6}$ alkyl can be also prepared, for example, by Synthetic method 5.

[Synthetic Method 5]

In the formula, $R^{1b}$ represents $C_{1-6}$ alkyl, $L^2$, n and $R^2$ have the same meanings as defined above.

Process 7

Compound (10) can be also prepared by allowing Compound (9) to react with a thioacetamide in an inert solvent under an acidic condition. As the inert solvent, tetrahydrofuran, dimethoxyethane, 1,4-dioxane, N,N-dimethylformamide, N-methylpyrrolidone, benzene, toluene, xylene, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 8

Compound (8a) can be also prepared by allowing Compound (10) to react with a 2-chloro-3-oxobutyric acid derivative in an inert solvent and optionally removing a protective group. As the inert solvent, methanol, ethanol, n-butanol, isopropanol, N,N-dimethylformamide, tetrahydrofuran, benzene, toluene and the like can be illustrated. The reaction temperature is usually at 0° C. to reflux temperature, and the reaction time is usually from 30 minutes to 7 days, varying based on a used starting material, solvent and reaction temperature or the like.

In Compound (8), Compound (8b) wherein ring U represents a thiazole ring, m is 1, $R^1$ represents $C_{1-6}$ alkyl and $L^2$ represents a trifluoromethansulfonyloxy group can be also prepared, for example, by Synthetic method 6.

[Synthetic Method 6]

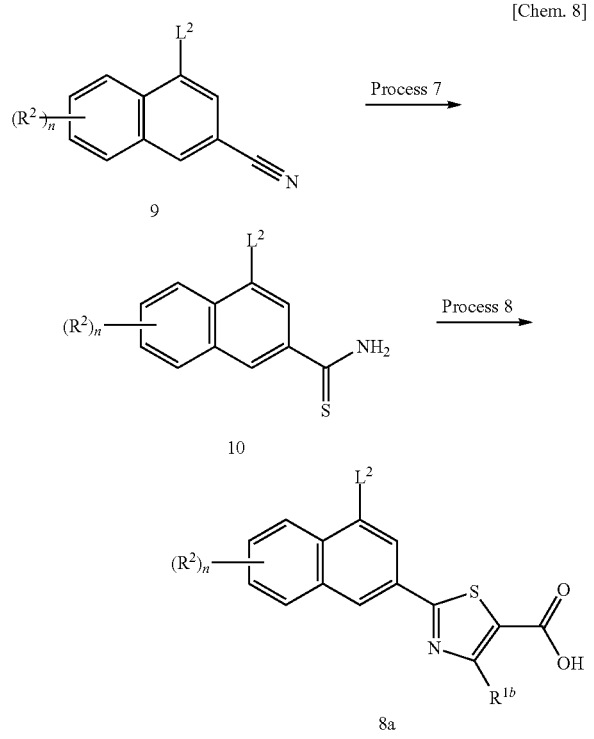

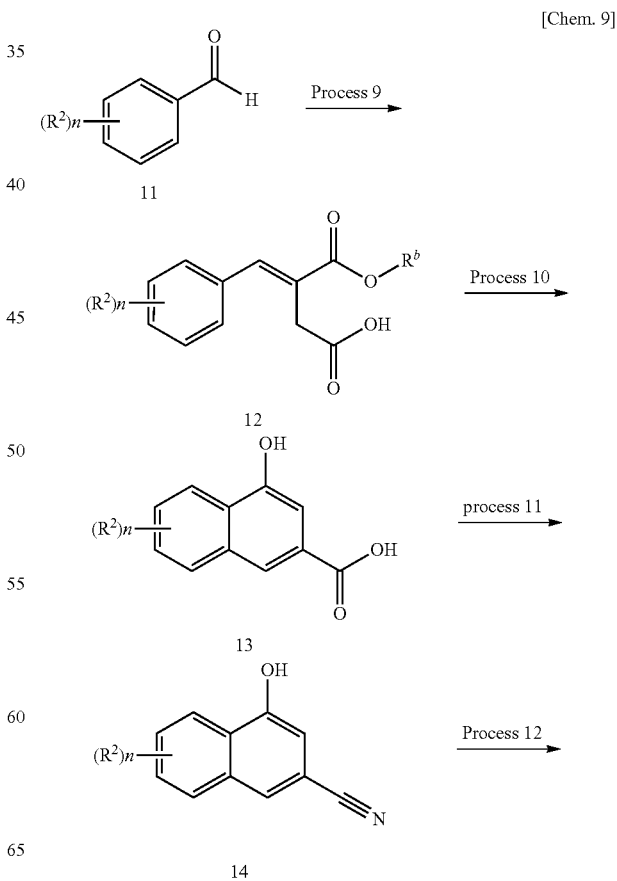

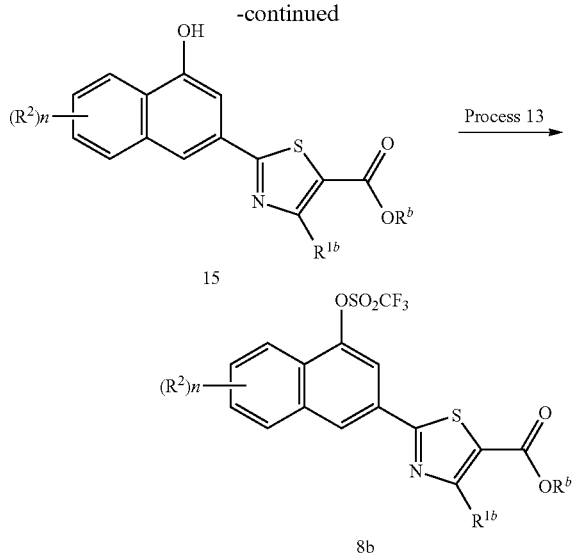

In the formula, $R^b$ represents $C_{1-6}$ alkyl, $R^{1b}$, n and $R^2$ have the same meanings as defined above.

Process 9

Compound (12) can be also prepared by subjecting Compound (11) to condensation with a Horner-Wadsworth-Emmons reagent such as 1-ethyl-4-tert-butyl-2-diethylphosphonosuccinate or the like and then removing a protective group, or by subjecting Compound (11) to condensation with diethyl succinate, in an inert solvent in the presence of a base. As the inert solvent, benzene, toluene, xylene, diethylether, tetrahydrofuran, 1,4-dioxane, 1,2-dimethoxyethane, N,N-dimethylformamide, N-methylpyrrolidone, methanol, ethanol, a mixed solvent thereof and the like can be illustrated. As the base, sodium hydride, potassium tert-butoxide, sodium methoxide, sodium ethoxide and the like can be illustrated. The reaction temperature is usually at 0° C. to reflux temperature, and the reaction time is usually from 30 minutes to 7 days, varying based on a used starting material, solvent and reaction temperature or the like.

Process 10

Compound (13) can be also prepared by allowing Compound (12) to react in an appropriate solvent in the presence of a dehydrating agent or in an acid anhydride solvent in the presence or absence of a base and optionally followed by hydrolyzation. As the appropriate solvent, for example, acetic acid, sulfuric acid, phosphoric acid, tetrahydrofuran, N,N-dimethylformamide, N-methylpyrrolidone, benzene, toluene, xylene, 1,4-dioxane, water, a mixed solvent thereof and the like can be illustrated. As the dehydrating agent, acetic anhydride, trifluoroacetic anhydride, methyl chloroformate, ethyl chloroformate and the like can be illustrated. As the acid anhydride solvent, acetic anhydride, trifluoroacetic anhydride and the like can be illustrated. As the base, sodium acetate, potassium acetate and the like can be illustrated. The reaction temperature is usually at room temperature to reflux temperature, and the reaction time is usually from 30 minutes to 7 days, varying based on a used starting material, solvent and reaction temperature or the like. As the inert solvent used in hydrolyzation, methanol, ethanol, isopropanol, tetrahydrofuran, N,N-dimethylformamide, N-methylpyrrolidone, dimethoxyethane, water and a mixed solvent thereof can be illustrated. As the base used in hydrolyzation, sodium hydroxide, potassium hydroxide and lithium hydroxide can be illustrated. The reaction temperature is usually at room temperature to reflux temperature, and the reaction time is usually from 30 minutes to 7 days, varying based on a used starting material, solvent and reaction temperature or the like.

Process 11

Compound (14) can be also prepared by subjecting Compound (13) to cyanation by a method similar to that as described in the above Processes 4 and 5.

Process 12

Compound (15) can be also obtained by allowing Compound (14) to react by a method similar to that as described in the above Processes 7 and 8.

Process 13

Compound (8b) can be prepared by allowing Compound (15) to react with a trifluoromethanesulfonic anhydride in an inert solvent in the presence of a base. As the inert solvent, dichloromethane, dichloroethane, chloroform, ethyl acetate, tetrahydrofuran, N,N-dimethylformamide, N-methylpyrrolidone, benzene, toluene, xylene, 1,4-dioxane and the like can be illustrated. As the base, triethylamine, N,N-diisopropylethylamine, pyridine, 2,6-lutidine, 1,8-diazabicyclo[5,4,0]-7-undecene and the like can be illustrated. The reaction temperature is usually at 0° C. to reflux temperature, and the reaction time is usually from 30 minutes to 7 days, varying based on a used starting material, solvent and reaction temperature or the like.

As the protective groups to be used in the present invention, various protective group generally used in organic reactions can be used. For example, as the protective groups of a hydroxy group, in addition to a p-methoxybenzyl group, a benzyl group, a methoxymethyl group, an acetyl group, a pivaloyl group, a benzoyl group, a tent-butyldimethylsilyl group, a tert-butyldiphenylsilyl group, an allyl group and the like, and when two hydroxy groups are adjacent, an isopropylidene group, a cyclopentylidene group, a cyclohexylidene group and the like can be illustrated. As the protective groups of a thiol group, a p-methoxybenzyl group, a benzyl group, an acetyl group, a pivaloyl group, a benzoyl group, a benzyloxycarbonyl group and the like can be illustrated. As the protective groups of an amino group, a benzyloxycarbonyl group, a tert-butoxycarbonyl group, a benzyl group, a p-methoxybenzyl group, a trifluoroacetyl group, an acetyl group, a phthaloyl group and the like can be illustrated. As the protective groups of a carboxy group, a $C_{1-6}$ alkyl group, a benzyl group, a tent-butyldimethylsilyl group, an allyl group and the like can be illustrated.

A compound represented by the formula (I) of the present invention can be isolated or purified by conventional isolation techniques, such as fractional recrystallization, purification by chromatography, solvent extraction, solid-phase extraction and the like.

A fused ring derivative represented by the formula (I) of the present invention can be converted into pharmaceutically acceptable salts thereof in the usual way. As such a salt, an acid additive salt with a mineral acid such as hydrochloric acid, hydrobromic acid, hydroiodic acid, sulfuric acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, an inorganic salt such as a sodium salt, a potassium salt, a calcium salt, a magnesium salt, a zinc salt, a lithium salt, an aluminum salt and the like, a salt with an organic amine such as N-methyl-D-glucamine, N,N'-dibenzylethylenediamine, 2-aminoethanol, tris(hydroxymethyl)aminomethane, arginine, lysine, piperazine, choline, diethylamine, 4-phenylcyclohexane and the like can be illustrated.

Among the fused ring derivatives represented by the formula (I) of the present invention, in a compound having an unsaturated bond, there are two geometrical isomers, a compound of cis (Z) form and a compound of trans (E) form. In the present invention, either of the compounds can be employed, and a mixture thereof can be also employed.

Among the fused ring derivatives represented by the formula (I) of the present invention, in a compound having a chiral carbon atom, there are a compound of R configuration and a compound of S configuration for each chiral carbon. In the present invention, either of the optical isomers can be employed, and a mixture of the optical isomers thereof can be also employed.

In the fused ring derivatives represented by the formula (I) of the present invention, there can be some tautomers, the compounds of the present invention also include these tautomers.

In the present invention, the term "prodrug" means a compound to be converted into a compound represented by the formula (I) within an organism. A prodrug of a compound represented by the formula (I) of the present invention can be prepared by introducing an appropriate group forming a prodrug into any one or more groups selected from a hydroxy group, an amino group, a carboxy group and other groups which can form a prodrug of the compound represented by the formula (I) using a corresponding reagent to produce a prodrug such as a halide compound or the like in the usual way, and then by suitably isolating and purifying in the usual way as occasion demands. See *Gekkan-Yakuji iyakuhin tekiseisiyou no tameno rinsyou yakubutsudoutai* (monthly pharmaceutical, clinical pharmacokinetics for the proper use of pharmaceutical products), 2000.3. extra edition, Vol. 42, No. 4, pp. 669-707, and *New Drug delivery system*, published by CMC Co., Ltd., 2000 Jan. 31., pp. 67-173. As a group forming a prodrug used in a hydroxy group or an amino group, for example, $C_{1-6}$ alkyl-CO— such as acetyl, propionyl, butyryl, isobutyryl, pivaloyl and the like; $C_6$ aryl-CO— such as benzoyl and the like; $C_{1-6}$ alkyl-O—$C_{1-6}$ alkylene-CO—; $C_{1-6}$ alkyl-OCO—$C_{1-6}$ alkylene-CO—; $C_{1-6}$ alkyl-OCO— such as methyloxycarbonyl, ethyloxycarbonyl, propyloxycarbonyl, isopropyloxycarbonyl, tert-butyloxycarbonyl and the like; $C_{1-6}$ alkyl-O—$C_{1-6}$ alkylene-OCO—; $C_{1-6}$ alkyl-COO—$C_{1-6}$ alkylene such as acetyloxymethyl, pivaloyloxymethyl, 1-(acetyloxy)ethyl, 1-(pivaloyloxy)ethyl and the like; $C_{1-6}$ alkyl-OCOO—$C_{1-6}$ alkylene such as methoxycarbonyloxymethyl, 1-(methoxycarbonyloxy)ethyl, ethoxycarbonyloxymethyl, 1-(ethoxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; $C_{3-8}$ cycloalkyl-OCOO—$C_{1-6}$ alkylene such as cyclohexyloxycarbonyloxymethyl, 1-(cyclohexyloxycarbonyl)ethyl and the like; an ester or an amide with an amino acid such as glycine and the like; and the like can be illustrated.

As a group forming a prodrug used in a carboxy group, for example, $C_{1-6}$ alkyl such as methyl, ethyl, propyl, isopropyl, butyl, tert-butyl and the like; $C_{1-6}$ alkyl-COO—$C_{1-6}$ alkylene such as pivaloyloxymethyl, acetyloxymethyl, 1-(pivaloyloxy)ethyl, 1-(acetyloxy)ethyl and the like; $C_{1-6}$ alkyl-OCOO—$C_{1-6}$ alkylene such as ethyloxycarbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxycarbonyloxy)ethyl and the like; $C_{3-8}$ cycloalkyl-OCOO—$C_{1-6}$ alkylene such as cyclohexyloxycarbonylmethyl, 1-(cyclohexyloxycarbonyl)ethyl and the like; and the like can be illustrated.

In the present invention, a pharmaceutically acceptable salt includes a solvate thereof with a pharmaceutically acceptable solvent such as water, ethanol or the like.

A pharmaceutical composition of the present invention is useful as an agent for the prevention or treatment of diseases associated with high blood uric acid levels such as hyperuricemia, gouty tophus, gouty arthritis, renal disorder associated with hyperuricemia, urinary calculi or the like, especially for hyperuricemia.

When a pharmaceutical composition of the present invention are employed in the practical prevention or treatment, the dosage of a compound represented by the formula (I) or a prodrug thereof or a pharmaceutically acceptable salt thereof as the active ingredient is appropriately decided depending on the age, sex, body weight, degree of disorders and treatment of each patient and the like, for example, which is approximately within the range of from 1 to 2,000 mg per day per adult human in the case of oral administration, and the daily dose can be divided into one to several doses per day and administered.

When a pharmaceutical composition of the present invention are employed in the practical prevention or treatment, various dosage forms are orally or parenterally used depending on their uses, for example, formulations for oral administration such as powders, fine granules, granules, tablets, capsules, dry syrups or the like is preferable.

These pharmaceutical compositions can be prepared depending on their formulations optionally by admixing using an appropriate pharmaceutical additive such as excipients, disintegrators, binders, lubricants and the like in accordance with conventional pharmaceutical methods, and formulating the mixture in accordance with conventional methods.

For example, powders can be formulated by, if desired, admixing well an active ingredient with appropriate excipients, lubricants and the like. For example, tablets can be formulated by tableting an active ingredient with appropriate excipients, disintegrators, binders, lubricants and the like in accordance with conventional methods, further if desired, can be suitably coated to provide film-coated tablets, sugar-coated tablets, enteric-coated tablets and the like. For example, capsules can be formulated by admixing well an active ingredient with appropriate excipients, lubricants and the like, or formulating fine granules, granules in accordance with conventional methods, and filling it in appropriate capsules. Furthermore, in the case of such an oral administration drug, it can be also formulated by conducting quick-release or sustained-release formulation depending on the preventions or the treatment methods.

A compound represented by the formula (I) of the present invention or a prodrug thereof, or a pharmaceutically acceptable salt thereof can be used further in combination with any other drug for the treatment of hyperuricemia or drug for the treatment of gout. As the drug for the treatment of hyperuricemia which can be used in the present invention, for example, urinary alkalizers such as sodium hydrogen carbonate, potassium citrate, sodium citrate and the like can be illustrated. In addition, as the drug for the treatment of gout, colchicine, or non-steroidal anti-inflammatory drugs such as indomethacin, naproxen, fenbufen, pranoprofen, oxaprozin, ketoprofen, etoricoxib, tenoxicam and the like and steroids and the like can be illustrated. In the present invention, an active ingredient of the present invention can be also used further in combination with at least one of these drugs, and a pharmaceutical composition comprising combination with at least one of these drugs includes any dosage forms of not only a single preparation comprising together with the active ingredient of the present invention but also a combination formulation consisting of a pharmaceutical composition comprising the active ingredient of the present invention and a separately-prepared pharmaceutical composition for simultaneous administration or administration at different dosage intervals. Furthermore, when used in combination with any drug other than the active ingredient of the present invention, the dosage of the fused ring derivative of the present invention can be reduced depending on the dosage of the other drug used in combination, as the case may be, an advantageous effect more than an additive effect in the prevention or treatment of the above diseases can be obtained, or an adverse effect of the other drug used in combination can be avoided or declined.

Effect of the Invention

The fused ring derivatives represented by the formula (I) of the present invention exert an excellent xanthine oxidase inhibitory activity and suppress the production of uric acid. In addition, a preferable compound of the present invention can also exert an excellent URAT1 inhibitory activity and enhance the uric acid excretion. Therefore, the fused ring derivatives represented by the formula (I) of the present invention or a prodrugs thereof, or pharmaceutically acceptable salts thereof can extremely suppress increase in serum uric acid level and are useful as an agent for the prevention or treatment of diseases associated with abnormal serum uric acid level such as hyperuricemia or the like.

BEST MODE TO OPERATE THE INVENTION

The present invention is further illustrated in more detail by way of the following Reference Examples, Examples and Test Examples. However, the present invention is not limited thereto.

Reference Example 1

3-Bromonaphthalene-1-carbonitrile

To a solution of 3-bromonaphthalene-1-carboxylic acid (0.30 g) in tetrahydrofuran (3 mL) was added 1,1'-carbonyldiimidazole (0.29 g) under ice-cooling, and the mixture was stirred at room temperature for 2 hours. To this reaction mixture was added ammonia water (1.0 mL, 28% aqueous solution), and the mixture was stirred at room temperature for 4 hours. The reaction mixture was concentrated under reduced pressure. To the residue was added water, and the mixture was stirred at room temperature for 15 minutes. The precipitated solid was collected by filtration. The obtained solid was washed with water and 1 mol/L hydrochloric acid, and dried to give 3-bromonaphthalene-1-carboxylic amide (0.28 g).

To a solution of the obtained compound (0.27 g) in dichloromethane (5 mL) were added triethylamine (0.44 g) and trifluoroacetic anhydride (0.47 g) under ice-cooling, and the mixture was stirred at room temperature for 6 hours. To the reaction mixture was added methanol, and the mixture was concentrated under reduced pressure. The obtained solid was collected by filtration, washed with water and n-hexane, and dried to give the title compound (0.22 g).

Reference Example 2

4-Cyano-2-naphthaleneboronic acid

To a solution of 3-bromonaphthalene-1-carbonitrile (0.69 g) and triisopropyl borate (0.89 g) in tetrahydrofuran (10 mL) was added n-butyl lithium (1.6 mL, 2.63 mol/L heptane solution) at −78° C. under an argon atmosphere. After warming to room temperature, the mixture was stirred at room temperature overnight. To the reaction mixture was added a saturated ammonium chloride aqueous solution at room temperature, and the mixture was extracted with ethyl acetate. The organic layer was washed with a saturated ammonium chloride aqueous solution and brine, dried over magnesium sulfate, and concentrated. The residue was suspended in n-hexane, and the solid was collected by filtration. The obtained solid was suspended in water. The suspension was acidified with hydrochloric acid, and the mixture was stirred for 30 minutes. The solid was collected by filtration, washed with water, and dried under reduced pressure to give the title compound (0.49 g).

Reference Example 3

2-Chloroquinoline-4-carbonitrile

The title compound was prepared in a similar manner to that described in Reference Example 1 using 2-chloroquinoline-4-carboxylic acid instead of 3-bromonaphthalene-1-carboxylic acid.

Reference Example 4

2-(4-Bromonaphthalene-2-yl)-4-methylthiazole-5-carboxylic acid ethyl ester

To a solution of 4-bromonaphthalene-2-carbonitrile (0.57 g) in N,N-dimethylformamide (4 mL) and 4 mol/L HCl 1,4-dioxane solution (4 mL) was added thioacetamide (1.1 g) at room temperature, and the reaction mixture was stirred at 70° C. overnight. The reaction mixture was poured into water, and the resulting mixture was extracted with ethyl acetate. The organic layer was washed with water and brine, dried over magnesium sulfate, and concentrated. The residue was purified by column chromatography on silica gel to give 4-bromonaphthalene-2-carbothioamide (0.48 g). To a suspension of this compound (0.48 g) in ethanol (6 mL) was added ethyl 2-chloro-acetoacetate (0.59 g), and the mixture was stirred at 65° C. for 24 hours. After cooling to room temperature, the precipitated solid was collected by filtration, washed with ethanol, and dried to give the title compound (0.41 g).

Reference Example 5

4-Hydroxy-6-methylnaphthalene-2-carboxylic acid

To a solution of 4-methylbenzaldehyde (0.70 g) and dimethyl succinate (0.95 g) in tetrahydrofuran (15 mL) was added potassium tert-butoxide (0.73 g) at room temperature, and the reaction mixture was stirred overnight. To the reaction mixture were added water and diethyl ether, and the two layers were separated. The aqueous layer was acidified with 1 mol/L hydrochloric acid, and the resulting mixture was extracted with diethyl ether. This organic layer was washed with a saturated sodium carbonate aqueous solution. The aqueous layer was acidified with 1 mol/L hydrochloric acid, and the mixture was extracted with diethyl ether. The organic layer was dried over magnesium sulfate, and concentrated. To the residue were added acetic acid (5 mL), acetic anhydride (5 mL) and sodium acetate (3.0 g), and the mixture was heated under reflux for 6 hours. After cooling to room temperature, the reaction mixture was poured into water. The resulting mixture was extracted with diethyl ether. The organic layer was washed with water and a saturated sodium hydrogen carbonate aqueous solution, and concentrated. To the obtained residue were added methanol (20 mL) and 1 mol/L sodium hydroxide aqueous solution (20 mL), and the mixture was heated under reflux for 5 hours. After the reaction mixture was cooled to room temperature, methanol was removed under reduced pressure. The obtained solution was acidified with 2 mol/L hydrochloric acid, and the resulting mixture was extracted with ethyl acetate. The organic layer was washed with water, dried over magnesium sulfate, and concentrated to give the title compound (0.20 g).

Reference Example 6

4-Hydroxy-6-methylnaphthalene-2-carbonitrile

The title compound was prepared in a similar manner to that described in Reference Example 1 using 4-hydroxy-6-methylnaphthalene-2-carboxylic acid (0.20 g) instead of 3-bromonaphthalene-1-carboxylic acid.

Reference Example 7

2-(4-Hydroxy-6-methylnaphthalene-2-yl)-4-methylthiazole-5-carboxylic acid ethyl ester The title compound was prepared in a similar manner to that described in Reference Example 4 using 4-hydroxy-6-methylnaphthalene-2-carbonitrile instead of 4-bromonaphthalene-2-carbonitrile.

Reference Example 8

2-(6-Chloro-4-hydroxynaphthalene-2-yl)-4-methylthiazole-5-carboxylic acid ethyl ester The title compound was prepared in a similar manner to that described in Reference Example 4 using 6-chloro-4-hydroxynaphthalene-2-carbonitrile instead of 4-bromonaphthalene-2-carbonitrile.

Reference Example 9

8-Bromo-4-hydroxy-7-methylnaphthalene-2-carboxylic acid

The title compound was prepared in a similar manner to that described in Reference Example 5 using the corresponding starting material.

Reference Example 10

4-Hydroxy-7-methylnaphthalene-2-carboxylic acid

To a solution of 8-bromo-4-hydroxy-7-methylnaphthalene-2-carboxylic acid (0.45 g) in ethanol (8 mL) was added palladium-carbon (180 mg) in 3 parts, and the mixture was stirred at room temperature for 2 days under a hydrogen atmosphere. The insoluble material was removed by filtering through a Celite pad, and the filtrate was concentrated to give the title compound (0.32 g).

Reference Example 11

2-(4-Hydroxy-7-methylnaphthalene-2-yl)-4-methylthiazole-5-carboxylic acid ethyl ester The title compound was prepared in a similar manner to that described in Reference Example 8 using the corresponding starting material.

Reference Example 12

4-Acetoxy-8-bromo-5-fluoronaphthalene-2-carboxylic acid methyl ester

To a solution of dimethyl succinate (4.6 g) in toluene (3.5 mL) was added sodium methoxide (28% methanol solution, 2.9 mL) at room temperature, and the mixture was stirred at 70° C. under an argon atmosphere. To this reaction mixture was added dropwise a solution of 2-bromo-5-fluorobenzaldehyde (3.0 g) in toluene (6.5 mL), and the mixture was stirred at 85° C. for 5 hours. After the reaction mixture was cooled to room temperature, diethyl ether was added to the mixture, and the mixture was poured into water. The aqueous layer was separated, and the organic layer was washed with water. The combined aqueous layer was acidified with 2 mol/L hydrochloric acid, and the resulting mixture was extracted with diethyl ether. The organic layer was washed with water and brine, dried over anhydrous magnesium sulfate, and concentrated. To the residue were added acetic anhydride (10 mL) and sodium acetate (3.7 g), and the mixture was stirred at 140° C. overnight. After the reaction mixture was cooled to room temperature, toluene (20 mL) was added to the mixture, and the mixture was concentrated under reduced pressure. To the residue was added 2 mol/L hydrochloric acid, and the resulting mixture was extracted with ethyl acetate. The organic layer was washed with water and brine, dried over magnesium sulfate, and concentrated. The residue was purified by column chromatography on silica gel (eluent: ethyl acetate/n-hexane) to give the title compound.

Reference Example 13

4-Acetoxy-5-fluoronaphthalene-2-carboxylic acid methyl ester

To a solution of 4-acetoxy-8-bromo-5-fluoronaphthalene-2-carboxylic acid methyl ester (2.0 g) and triethylamine (0.72 g) in ethyl acetate (60 mL) was added palladium-carbon (600 mg) at room temperature, and the mixture was stirred for 1 hour at the same temperature under a hydrogen atmosphere. The insoluble material was removed by filtering through a Celite pad, and the filtrate was concentrated under reduced pressure. The residue was purified by column chromatography on silica gel (eluent: ethyl acetate/n-hexane) to give the title compound.

Reference Example 14

4-Hydroxynaphthalene-2-carbonitrile

The title compound was prepared in a similar manner to that described in Reference Example 6 using the corresponding starting material.

Reference Example 15

3-(4-Hydroxynaphthalene-2-yl)-[1,2,4]oxadiazole-5-carboxylic acid ethyl ester

A mixed solution of 4-hydroxynaphthalene-2-carbonitrile (0.34 g), hydroxylamine hydrochloride (0.14 g) and potassium carbonate (0.30 g) in tert-butylalcohol (4.5 mL) and water (0.5 mL) was stirred at 80° C. for 6 hours. To the reaction mixture was added hydroxylamine hydrochloride (0.14 g), and the mixture was stirred at room temperature for 1 hour. The reaction solution was diluted with ethyl acetate, and washed with water and brine. The organic layer was dried over anhydrous magnesium sulfate, and concentrated under reduced pressure. The residue was purified by column chromatography on silica gel (eluent: dichloromethane/methanol). This compound (0.22 g) was dissolved in dichloromethane (5.3 mL). To the mixture were added ethyl oxalyl chloride (0.35 mL) and pyridine (0.52 mL), and the mixture was stirred at room temperature for 1.5 hours. To the reaction solution was added water, and the organic layer was washed with water and a saturated sodium hydrogen carbonate aqueous solution. The organic layer was dried over anhydrous magnesium sulfate, and concentrated under reduced pressure. The residue was purified by column chromatography on silica gel (eluent: hexane/ethyl acetate) to give the title compound (0.15 g).

Reference Example 16

3-(4-Bromonaphthalene-2-yl)-[1,2,4]thiadiazole-5-carboxylic acid ethyl ester

To a solution of 4-bromonaphthalene-2-carboxylic amide (1.10 g) in toluene (11.0 mL) was added chlorocarbonylsulfenyl chloride (0.73 mL), and the mixture was stirred at 100° C. for 18 hours. To the reaction solution was added water (50 mL). The precipitated solid was collected by filtration, and washed with water and hexane to give 5-(4-bromonaphthalene-2-yl)-[1,3,4]oxathiazole-2-one (1.13 g). This compound (1.12 g) was dissolved in dichlorobenzene (18 mL). To the solution was added ethyl cyanoformate (1.42 mL), and the mixture was stirred at 160° C. for 22 hours. To the mixture was added water (30 mL) at room temperature, and the resulting mixture was extracted with dichloromethane. The organic layer was washed with brine, dried over anhydrous magnesium sulfate, and concentrated under reduced pressure. The residue was purified by column chromatography on silica gel (eluent: hexane/ethyl acetate) to give the title compound (1.21 g).

Reference Example 17

3-(4-Bromonaphthalene-2-yl)isothiazole-5-carboxylic acid ethyl ester

To a solution of 4-bromonaphthalene-2-carboxylic amide (1.10 g) in toluene (11.0 mL) was added chlorocarbonylsulfenyl chloride (0.73 mL), and the mixture was stirred at 100° C. for 18 hours. To the reaction solution was added water (50 mL), and the precipitated solid was collected by filtration. The obtained solid was washed with water and hexane to give 5-(4-bromonaphthalene-2-yl)-[1,3,4]oxathiazole-2-one (1.13 g). This compound (1.13 g) was dissolved in dichlorobenzene (18 mL). To the solution was added ethyl propiolate (1.52 mL), and the mixture was stirred at 160° C. for 18 hours. The reaction solution was purified by column chromatography on silica gel (eluent: hexane/ethyl acetate) to give the title compound (0.66 g).

Reference Example 18

4-Cyanonaphthalene-2-carboxylic acid

To a solution of 4-hydroxynaphthalene-2-carboxylic acid ethyl ester (2.16 g) and pyridine (1.60 mL) in dichloromethane (100 mL) was added trifluoromethanesulfonic anhydride (2.5 mL) under ice-cooling, and the mixture was stirred at the same temperature for 10 minutes. To the reaction solution was added water (30 mL), and the resulting mixture was extracted with diethyl ether. The organic layer was washed with brine, dried over anhydrous magnesium sulfate, and concentrated under reduced pressure. The residue was dissolved in N-methylpyrrolidone (33 mL). To the solution were added zinc cyanide (1.41 g) and tetrakis(triphenylphosphine)palladium (0.58 g), and the resulting mixture was stirred at 110° C. for 40 minutes. After the reaction mixture was cooled to room temperature, water (50 ml) and dichloromethane (50 mL) were added to the reaction solution. The insoluble material was removed by filtering through a Celite pad. The aqueous layer was separated, and the organic layer was filtered through an aminopropyl silica gel (eluent: dichloromethane). The organic layer was concentrated under reduced pressure. To the residue was added ethyl acetate (20 mL), and the mixture was washed with water (30 mL, 5 times). The organic layer was dried over anhydrous magnesium sulfate, and concentrated under reduced pressure. The obtained residue was purified by column chromatography on silica gel (eluent: hexane/ethyl acetate) to give 4-cyanonaphthalene-2-carboxylic acid ethyl ester (2.25 g). To a mixed solution of this compound (0.45 g) in tetrahydrofuran (10 mL), ethanol (5.0 mL) and water (5.0 mL) was added lithium hydroxide monohydrate (0.25 g), and the mixture was stirred for 1 hour. To the reaction solution was added water (20 mL), and the resulting mixture was washed with diethyl ether. To the aqueous layer was added 1 mol/L hydrochloric acid (3.3 mL), and the precipitated solid was collected by filtration. The obtained solid was dried under reduced pressure at 50° C. to give the title compound (0.37 g).

Reference Example 19

2-(4-Cyanonaphthalene-2-yl)-4-methyloxazole-5-carboxylic acid methyl ester

To a solution of 4-cyanonaphthalene-2-carboxylic acid (0.37 g) in dichloromethane (20 mL) were added dimethylformamide (5 drops) and oxalyl dichloride (0.5 mL) under ice-cooling, and the mixture was stirred at room temperature for 30 minutes. The solvent was removed under reduced pressure. To the residue was added toluene (10 mL), and the mixture was concentrated under reduced pressure. To a solution of 2-aminopropionic acid ethyl ester hydrochloride (0.29 g) and triethylamine (0.66 mL) in dichloromethane (10 mL) was added dropwise the obtained residue under ice-cooling, and the mixture was stirred at room temperature for 30 minutes. To the mixture were added water and 1 mol/L hydrochloric acid (1.56 mL). The aqueous layer was separated, and the organic layer was washed with a saturated sodium hydrogen carbonate aqueous solution, water and brine. The organic layer was dried over anhydrous magnesium sulfate, and concentrated under reduced pressure. The obtained residue was purified by column chromatography on silica gel (eluent: hexane/ethyl acetate) to give ethyl 2-[(4-cyanonaphthalene-2-carbonyl)amino]-propionate (0.43 g). To a solution of this compound (0.43 g) in tetrahydrofuran (10 mL) was added 1 mol/L sodium hydroxide aqueous solution (3.8 mL), and the mixture was stirred for 30 minutes. To the mixture was added 1 mol/L hydrochloric acid (4.4 mL) under ice-cooling, and the resulting mixture was extracted with ethyl acetate. The organic layer was dried over anhydrous magnesium sulfate, and concentrated under reduced pressure to give 2-[(4-cyanonaphthalene-2-carbonyl)amino]propionic acid (0.39 g). To a solution of this compound (0.39 g) in dichloromethane (7.0 mL) were added dimethylformamide (2 drops) and oxalyl dichloride (1.26 mL), and the mixture was stirred at room temperature for 30 minutes. The solvent was removed under reduced pressure. To the residue was added toluene (10 mL), and the mixture was concentrated under reduced pressure. After the obtained residue was dissolved in dichloromethane (7.0 mL), triethylamine (0.31 mL) and methanol (1.0 mL) were added to the mixture under ice-cooling. The mixture was stirred at room temperature for 16 hours, and the solvent was removed under reduced pressure. The obtained residue was purified by column chromatography on silica gel (eluent: hexane/ethyl acetate) to give the title compound (0.045 g).

Reference Example 20

4-Acetoxy-8-bromo-5,6-difluoronaphthalene-2-carboxylic acid methyl ester

The title compound was prepared in a similar manner to that described in Reference Example 12 using 2-bromo-4,5-difluorobenzaldehyde instead of 2-bromo-5-fluorobenzaldehyde.

Reference Example 21

5-Fluoro-2-iodo-3-methylbenzaldehyde

To a solution of 5-fluoro-2-iodo-3-methyl-benzoic acid methyl ester (11.2 g) in dichloromethane (80 mL) was added dropwise over 25 minutes diisobutyl aluminium hydride (113 mL, 1.02 mol/L hexane solution) at −78° C., and the mixture was stirred at the same temperature for 30 minutes. To the reaction mixture was added dropwise methanol (10 mL) at the same temperature, and the mixture was stirred for 10 minutes. To the reaction mixture was added a saturated potassium sodium tartrate tetrahydrate aqueous solution (300 mL) under ice-cooling, and the mixture was stirred for 30 minutes. The reaction mixture was extracted with ethyl acetate. The organic layer was washed with brine, dried over anhydrous magnesium sulfate, and concentrated under reduced pressure. The residue was washed with hexane to give (5-fluoro-2-iodo-3-methyl-phenyl)methanol (7.15 g). To a suspension of the obtained compound (7.15 g) in chloroform (53 mL) and acetone (5.2 mL) was added manganese dioxide, and the mixture was stirred at room temperature for 4 hours. The reaction mixture was filtered through a Celite pad, and the filtrate was concentrated. The residue was purified by column chromatography on silica gel (eluent: ethyl acetate/n-hexane=0-15%) to give the title compound (3.54 g).

Reference Example 22

4-Acetoxy-5-fluoro-8-iodo-7-methylnaphthalene-2-carboxylic acid methyl ester

The title compound was prepared in a similar manner to that described in Reference Example 12 using 5-fluoro-2-iodo-3-methylbenzaldehyde instead of 2-bromo-5-fluorobenzaldehyde.

Reference Examples 23 to 24

4-Acetoxy-5,6-difluoronaphthalene-2-carboxylic acid methyl ester

4-Acetoxy-5-fluoro-7-methylnaphthalene-2-carboxylic acid methyl ester

The title compounds were prepared in a similar manner to that described in Reference Example 13 using the corresponding starting materials.

Reference Examples 25 to 43

The compounds of Reference Examples 25 to 43 were prepared in a similar manner to that described in Reference Example 6 using the corresponding starting materials.

Reference Examples 44 to 62

The compounds of Reference Examples 44 to 62 were prepared in a similar manner to that described in Reference Example 7 using the corresponding starting materials.

Reference Example 63

2-(4-Hydroxynaphthalene-2-yl)thiazole-5-carboxylic acid ethyl ester

The title compound was prepared in a similar manner to that described in Reference Example 7 using ethyl 2-chloro-oxopropionate instead of ethyl 2-chloro-acetoacetate.

Reference Examples 64 to 75

The compounds of Reference Examples 64 to 75 were prepared in a similar manner to that described in Reference Example 63 using the corresponding starting materials.

Example 1

2-(4-Cyanonaphthalene-2-yl)isonicotinic acid

To a suspension of 4-cyano-2-naphthaleneboronic acid (0.10 g), 2-bromoisonicotinic acid ethyl ester (0.12 g) and cesium fluoride (0.09 g) in dimethoxyethane (6 mL) was added tetrakis(triphenylphosphine)palladium (0.06 g), and the mixture was stirred at 150° C. for 40 minutes using microwave reactor (Biotage). The reaction mixture was filtered through a Celite pad, and the filtrate was concentrated under reduced pressure. The residue was purified by column chromatography on silica gel (eluent: n-hexane/ethyl acetate=100/0-66/34) to give 2-(4-cyanonaphthalene-2-yl)isonicotinic acid ethyl ester (0.14 g). To a solution of this compound (0.14 g) in a mixed solvent of tetrahydrofuran (4 mL), ethanol (1 mL) and water (1 mL) was added lithium hydroxide monohydrate (0.060 g), and the mixture was stirred at room temperature overnight. To the reaction mixture was added acetic acid (0.27 mL). The precipitated solid was collected by filtration, and washed with water and n-hexane. The solid was dried under reduced pressure to give the title compound (0.098 g).

Example 2

2-(4-Cyanonaphthalene-2-yl)-5-hydroxyisonicotinic acid 2-(4-Cyanonaphthalene-2-yl)-5-methoxymethoxyisonicotinic acid ethyl ester (0.12 g) was obtained in a similar manner to that described in Example 1 using 2-bromo-5-methoxymethoxyisonicotinic acid ethyl ester instead of 2-bromoisonicotinic acid ethyl ester. To a mixed solution of this compound in tetrahydrofuran (4 mL), ethanol (1 mL) and water (1 mL) was added lithium hydroxide monohydrate (0.043 g), and the mixture was stirred at room temperature overnight. To this reaction mixture was added 2 mol/L hydrochloric acid (1 mL), and the mixture was stirred at 50° C. for 8 hours. After the reaction mixture was cooled to room temperature, the precipitated solid was collected by filtration, and dried under reduced pressure to give the title compound (0.087 g).

Example 3

1-(4-Cyanonaphthalene-2-yl)-1H-pyrazole-3-carboxylic acid

A suspension of 1H-pyrazole-3-carboxylic acid ethyl ester (0.1 g), 3-bromonaphthalene-1-carbonitrile (0.17 g), copper iodide (0.0068 g), (1R,2R)-(−)-N, N'-dimethylcyclohexane-1,2-diamine (0.010 g) and potassium carbonate (0.21 g) in toluene (3 mL) was stirred at 90° C. overnight. After cooling to room temperature, ethyl acetate was added to the reaction mixture. The resulting mixture was filtered through a Celite pad. The residue was purified by column chromatography on silica gel (eluent: n-hexane/ethyl acetate=100/0-66/34) to give 1-(4-cyanonaphthalene-2-yl)-1H-pyrazole-3-carboxylic acid ethyl ester (0.040 g). To a solution of this compound (0.040 g) in a mixed solvent of tetrahydrofuran (0.2 mL), ethanol (0.08 mL) and water (0.08 mL) was added lithium hydroxide monohydrate (0.017 g), and the mixture was stirred at room temperature overnight. To the reaction mixture was added 2 mol/L hydrochloric acid (0.35 mL). The precipitated solid was collected by filtration, washed with water and n-hexane, and dried under reduced pressure to give the title compound (0.026 g).

Example 4

4-(4-Cyanonaphthalene-2-yl)benzoic acid

4-Methoxycarbonylphenylboronic acid (0.039 g), 3-bromonaphthalene-1-carbonitrile (0.05 g), tetrakis(triphenylphosphine)palladium (0.012 g) and cesium carbonate (0.11 g) were suspended in a mixed solvent of N,N-dimethylformamide (3 mL) and water (1 mL), and the resulting mixture was stirred at 150° C. for 40 minutes using microwave reactor (Biotage). The reaction mixture was poured into water, and the resulting mixture was extracted with ethyl acetate. The organic layer was concentrated under reduced pressure, and the residue was purified by column chromatography on silica gel (eluent: n-hexane/ethyl acetate=100/0-66/34) to give 4-(4-cyanonaphthalene-2-yl)benzoic acid methyl ester (0.025 g).

The title compound (0.020 g) was prepared in a similar manner to that described in Example 3 using 4-(4-cyanonaphthalene-2-yl)benzoic acid methyl ester instead of 1-(4-cyanonaphthalene-2-yl)-1H-pyrazole-3-carboxylic acid ethyl ester.

Example 5

4-(4-Cyanoquinoline-2-yl)benzoic acid

2-Chloroquinoline-4-carbonitrile (0.20 g), 4-methoxycarbonylphenylboronic acid (0.21 g), tetrakis(triphenylphosphine)palladium (0.061 g) and sodium carbonate (0.22 g) were suspended in a mixed solvent of dimethoxyethane (2 mL) and water (0.5 mL), and the resulting mixture was stirred at 150° C. for 30 minutes using microwave reactor (Biotage). To the reaction mixture was added ethyl acetate, and the reaction mixture was filtered through a Celite pad. The filtrate was poured into water, and the organic layer was washed with water and brine. The organic layer was concentrated under reduced pressure. The residue was purified by column chromatography on silica gel (eluent: n-hexane/ethyl acetate=100/0-66/34) to give 4-(4-cyanonaphthalene-2-yl) benzoic acid methyl ester (0.12 g). To a solution of this compound (0.12 g) in a mixed solvent of tetrahydrofuran (2 mL), ethanol (1 mL) and water (1 mL) was added lithium hydroxide monohydrate (0.14 g), and the mixture was stirred at room temperature overnight. To the reaction mixture was added 2 mol/L hydrochloric acid (0.35 mL). The precipitated solid was collected by filtration, washed with methanol, and dried under reduced pressure to give the title compound (0.024 g).

Example 6

4-(4-Cyanoquinoline-2-yl)-2-hydroxy-benzoic acid

2-Chloroquinoline-4-carbonitrile (0.15 g), 2-methoxymethoxy-4-(4,4,5,5-tetramethyl-[1,3,2]dioxaborolane-2-yl)benzoic acid methyl ester (0.26 g), tetrakis(triphenylphosphine)palladium (0.045 g) and sodium carbonate (0.16 g) were suspended in a mixed solvent of dimethoxyethane (2 mL) and water (0.5 mL), and the resulting mixture was stirred at 150° C. for 30 minutes using microwave reactor (Biotage). To the reaction mixture was added ethyl acetate, and the mixture was filtered through a Celite pad. The filtrate was poured into water. The organic layer was washed with water and brine, and concentrated under reduced pressure. The residue was purified by column chromatography on silica gel (eluent: n-hexane/ethyl acetate=100/0-66/34) to give 4-(4-cyanoquinoline-2-yl)-2-hydroxy-benzoic acid methyl ester (0.1 g). To a mixed solution of this compound (0.1 g) in tetrahydrofuran (4 mL), ethanol (1 mL) and water (1 mL) was added lithium hydroxide monohydrate (0.060 g), and the mixture was stirred at room temperature overnight. To this reaction mixture was added 2 mol/L hydrochloric acid (2.8 mL), and the mixture was stirred at 50° C. for 10 hours. After the reaction mixture was cooled to room temperature, the precipitated solid was collected by filtration, and dried under reduced pressure to give the title compound (0.068 g).

Example 7

2-(4-Cyanonaphthalene-2-yl)-4-methylthiazole-5-carboxylic acid

A suspension of 2-(4-bromonaphthalene-2-yl)-4-methylthiazole-5-carboxylic acid ethyl ester (0.050 g), zinc cyanide (0.031 g) and tetrakis(triphenylphosphine)palladium (0.015 g) in N-methylpyrrolidone (2 mL) was stirred at 150° C. for 50 minutes using microwave reactor (Biotage). To the reaction mixture was added water (15 mL), and the precipitated solid was collected by filtration, and washed with water and n-hexane to give 2-(4-cyanonaphthalene-2-yl)-4-methylthiazole-5-carboxylic acid ethyl ester (0.042 g).

The title compound (0.035 g) was prepared in a similar manner to that described in Example 6 using 2-(4-cyanonaphthalene-2-yl)-4-methylthiazole-5-carboxylic acid ethyl ester instead of 4-(4-cyanoquinoline-2-yl)-2-hydroxy-benzoic acid methyl ester.

Example 8

2-(4-Cyano-6-methylnaphthalene-2-yl)-4-methylthiazole-5-carboxylic acid

To a suspension of 2-(4-hydroxy-6-methylnaphthalene-2-yl)-4-methylthiazole-5-carboxylic acid ethyl ester (0.030 g) in dichloromethane (2 mL) were added pyridine (0.058 g) and trifluoromethanesulfonic anhydride (0.10 g) at room temperature, and the mixture was stirred for 2 hours. The reaction mixture was poured into 1 mol/L hydrochloric acid (4 mL), and the resulting mixture was extracted with diethyl ether. The organic layer was washed with water and brine, and dried over magnesium sulfate to give 4-methyl-2-(6-methyl-4-trifluoromethanesulfonyloxynaphthalene-2-yl)thiazole-5-carboxylic acid ethyl ester. To a solution of the obtained compound in N-methylpyrrolidone were added zinc cyanide (0.043 g) and tetrakis(triphenylphosphine)palladium (0.021 g) at room temperature, and the mixture was stirred at 150° C. for 40 minutes using microwave reactor (Biotage). To the reaction mixture was added water, and the precipitated solid was collected by filtration. This solid was washed with water, and purified by column chromatography on aminopropylsilica gel (eluent: ethyl acetate) to give 2-(4-cyano-6-methylnaphthalene-2-yl)-4-methylthiazole-5-carboxylic acid ethyl ester (0.022 g). To a mixed solution of this compound (0.022 g) in tetrahydrofuran (2 mL), ethanol (0.5 mL) and water (0.5 mL) was added lithium hydroxide monohydrate (0.008 g), and the mixture was stirred at room temperature overnight. To this reaction mixture was added water (2 mL), and the resulting mixture was extracted with diethyl ether. To the aqueous layer was added 1 mol/L hydrochloric acid (2 mL), and the resulting mixture was extracted with ethyl acetate (8 mL). The organic layer was washed with water and brine, dried over magnesium sulfate, and concentrated to give the title compound (0.012 g).

Examples 9 to 10

The compounds of Examples 9 to 10 were prepared in a similar manner to that described in Example 8 using the corresponding starting materials.

Examples 11 to 44

The compounds of Examples 11 to 44 were prepared in a similar manner to that described in Example 8 using the corresponding starting materials.

Examples 45 to 46

The compounds of Examples 45 to 46 were prepared in a similar manner to that described in Example 7 using the corresponding starting materials.

Example 47

2-(4-Cyanonaphthalene-2-yl)-4-methyloxazole-5-carboxylic acid

To a mixed solution of 2-(4-cyanonaphthalene-2-yl)-4-methyloxazole-5-carboxylic acid methyl ester (0.045 g) in tetrahydrofuran (1.5 mL), ethanol (0.8 mL) and water (0.8 mL) was added lithium hydroxide monohydrate (0.02 g), and the mixture was stirred for 30 minutes. To the reaction solution was added water, and the resulting mixture was washed with diethyl ether. To the aqueous layer was added 1 mol/L hydrochloric acid (0.5 mL). The precipitated solid was collected by filtration, and dried under reduced pressure to give the title compound (0.028 g).

Example 48

2-(4-Cyano-8-fluoro-7-hydroxynaphthalene-2-yl)-4-methylthiazole-5-carboxylic acid To a suspension of 2-(4-cyano-8-fluoro-7-methoxynaphthalene-2-yl)-4-methylthiazole-5-carboxylic acid (0.22 g) in dichloromethane (1 mL) was added boron tribromide (1 mol/L dichloromethane solution, 128 μL) under methanol-ice-cooling, and the mixture was stirred at room temperature for 30 minutes, followed by stirring with heating at 40° C. for 2.5 hours. After cooling to room temperature, to the mixture was added 1 mol/L hydrochloric acid. The precipitated crystal was collected by filtration, and dried under reduced pressure at 50° C. to give the title compound (0.018 g).

Example 49

2-(4-Cyano-7-hydroxynaphthalene-2-yl)-4-methylthiazole-5-carboxylic acid

To a suspension of 2-(7-benzyloxy-4-cyanonaphthalene-2-yl)-4-methylthiazole-5-carboxylic acid ethyl ester (0.27 g) in tetrahydrofuran (20 mL) was added palladium-carbon (100 mg) at room temperature, and the mixture was stirred at the same temperature for 1.5 hours under a hydrogen atmosphere. The mixture was stirred at 50° C. overnight. The reaction mixture was filtered through a Celite pad, and the filtrate was concentrated under reduced pressure. The residue was suspended in ethyl acetate, and the resulting mixture was filtered. The filtrate was concentrated under reduced pressure. The residue was purified by column chromatography on silica gel (eluent: hexane/ethyl acetate=95/5-40/60) to give 2-(4-cyano-7-hydroxynaphthalene-2-yl)-4-methylthiazole-5-carboxylic acid ethyl ester (0.067 g). The title compound (0.019 g) was prepared by deprotecting this compound (0.030 g) in a similar manner to that described in Example 47.

Tables 1 to 10 show the chemical structures of the above compounds of Reference Examples 25 to 75, and the chemical structures and $^1$H-NMR data of the compounds of Examples 1 to 49.

The abbreviations in these Tables: "Ref No.", "Ex No.", "Strc." and "Sols.", represent Reference Example number, Example number, chemical structure and measurement solvent of $^1$H-NMR, respectively.

TABLE 1

| Ref No | Strc. |
|---|---|
| 25 | 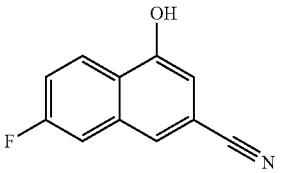 |
| 26 | 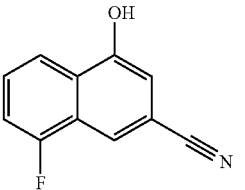 |
| 27 | 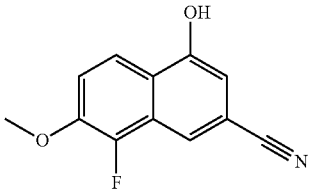 |
| 28 | 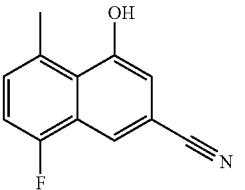 |
| 29 | 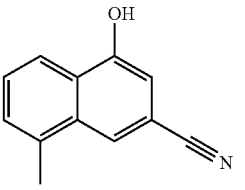 |
| 30 | 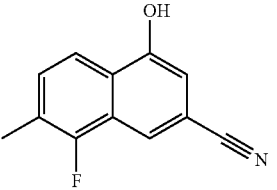 |
| 31 | 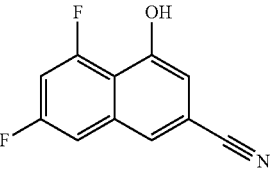 |

TABLE 1-continued

| Ref No | Strc. |
|---|---|
| 32 | 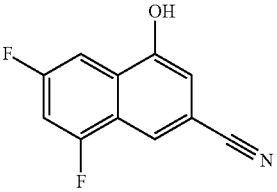 |
| 33 | 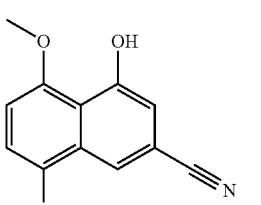 |
| 34 | 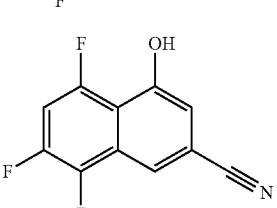 |
| 35 | 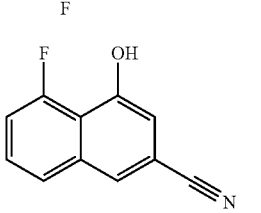 |
| 36 | 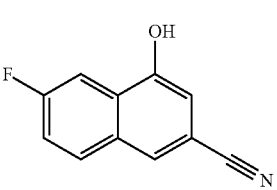 |
| 37 | 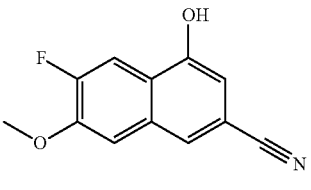 |
| 38 | 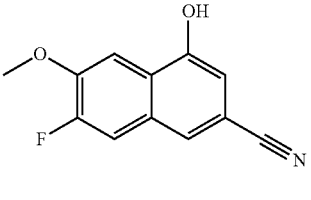 |
| 39 | 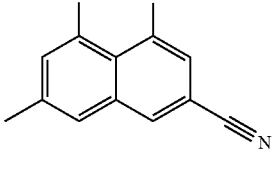 |

TABLE 1-continued

| Ref No | Strc. |
|---|---|
| 40 | 6,7-difluoro-4-hydroxy-naphthalene-2-carbonitrile |
| 41 | 7-benzyloxy-4-hydroxy-naphthalene-2-carbonitrile |
| 42 | 6-fluoro-4-hydroxy-8-methyl-naphthalene-2-carbonitrile |
| 43 | 7,8-difluoro-4-hydroxy-naphthalene-2-carbonitrile |

TABLE 2

| Ref No | Strc. |
|---|---|
| 44 | ethyl 2-(7-fluoro-4-hydroxy-naphthalen-2-yl)-4-methyl-thiazole-5-carboxylate |
| 45 | ethyl 2-(8-fluoro-4-hydroxy-naphthalen-2-yl)-4-methyl-thiazole-5-carboxylate |
| 46 | ethyl 2-(8-fluoro-7-methoxy-4-hydroxy-naphthalen-2-yl)-4-methyl-thiazole-5-carboxylate |
| 47 | ethyl 2-(8-fluoro-5-methyl-4-hydroxy-naphthalen-2-yl)-4-methyl-thiazole-5-carboxylate |
| 48 | ethyl 2-(5-methyl-4-hydroxy-naphthalen-2-yl)-4-methyl-thiazole-5-carboxylate |
| 49 | ethyl 2-(8-fluoro-7-methyl-4-hydroxy-naphthalen-2-yl)-4-methyl-thiazole-5-carboxylate |
| 50 | ethyl 2-(6,8-difluoro-4-hydroxy-naphthalen-2-yl)-4-methyl-thiazole-5-carboxylate |
| 51 | ethyl 2-(5,7-difluoro-4-hydroxy-naphthalen-2-yl)-4-methyl-thiazole-5-carboxylate |

TABLE 2-continued

| Ref No | Strc. |
|---|---|
| 52 | (structure) |
| 53 | (structure) |
| 54 | (structure) |
| 55 | (structure) |
| 56 | (structure) |
| 57 | (structure) |

TABLE 2-continued

| Ref No | Strc. |
|---|---|
| 58 | (structure) |
| 59 | (structure) |

TABLE 3

| Ref No | Strc. |
|---|---|
| 60 | (structure) |
| 61 | (structure) |
| 62 | (structure) |

TABLE 3-continued

| Ref No | Strc. |
|---|---|
| 63 | *ethyl 2-(4-hydroxynaphthalen-2-yl)thiazole-5-carboxylate* |
| 64 | *ethyl 2-(8-fluoro-4-hydroxynaphthalen-2-yl)thiazole-5-carboxylate* |
| 65 | *ethyl 2-(8-fluoro-7-methoxy-4-hydroxynaphthalen-2-yl)thiazole-5-carboxylate* |
| 66 | *ethyl 2-(8-fluoro-5-methyl-4-hydroxynaphthalen-2-yl)thiazole-5-carboxylate* |
| 67 | *ethyl 2-(8-fluoro-6-methyl-4-hydroxynaphthalen-2-yl)thiazole-5-carboxylate* |
| 68 | *ethyl 2-(6,8-difluoro-4-hydroxynaphthalen-2-yl)thiazole-5-carboxylate* |
| 69 | *ethyl 2-(5,7-difluoro-4-hydroxynaphthalen-2-yl)thiazole-5-carboxylate* |
| 70 | *ethyl 2-(8-fluoro-5-methoxy-4-hydroxynaphthalen-2-yl)thiazole-5-carboxylate* |
| 71 | *ethyl 2-(5,6,8-trifluoro-4-hydroxynaphthalen-2-yl)thiazole-5-carboxylate* |
| 72 | *ethyl 2-(5-fluoro-4-hydroxynaphthalen-2-yl)thiazole-5-carboxylate* |
| 73 | *ethyl 2-(6-fluoro-7-methoxy-4-hydroxynaphthalen-2-yl)thiazole-5-carboxylate* |
| 74 | *ethyl 2-(6-fluoro-8-methyl-4-hydroxynaphthalen-2-yl)thiazole-5-carboxylate* |

TABLE 3-continued
| Ref No | Strc. |
|---|---|
| 75 | 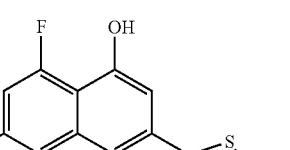 |
TABLE 4
| Ex No. | Strc | $^1$H-NMR δ ppm (DMSO-d6) |
|---|---|---|
| 1 | | 7.75-7.95 (3H, m), 8.10-8.15 (1H, m), 8.33 (1H, d, J = 8.2 Hz) 8.60-8.65 (1H, m), 8.90-9.00 (2H, m), 9.15-9.20 (1H, m) |
| 2 | | 7.70-7.85 (2H, m), 8.10-8.15 (1H, m), 8.20-8.30 (1H, m), 8.41 (1H, s), 8.54 (1H, s), 8.83 (1H, d, J = 1.8 Hz), 8.95-9.05 (1H, m) |
| 3 | | 7.75-7.90 (2H, m), 8.10-8.30 (3H, m), 8.83 (1H, d, J = 2.3 Hz), 8.85-8.95 (1H, m), 9.28 (1H, s), 12.81 (1H, brs.) |
| 4 | | 7.75-7.90 (2H, m), 8.00-8.30 (6H, m), 8.64 (1H, d, J = 1.9 Hz), 8.75-8.80 (1H, m) |
TABLE 4-continued
| Ex No. | Strc | $^1$H-NMR δ ppm (DMSO-d6) |
|---|---|---|
| 5 | | 7.80-8.60 (6H, m), 8.48 (2H, d, J = 8.2 Hz), 8.92 (1H, s) |
| 6 | | 7.85-8.05 (5H, m), 8.10-8.15 (1H, m), 8.25-8.30 (1H, m), 8.89 (1H, s), 11.38 (1H, brs.) |
| 7 | | 2.73 (3H, s), 7.75-8.00 (2H, m), 8.16 (1H, d, J = 8.3 Hz), 8.33 (1H, d, J = 8.2 Hz), 8.68 (1H, d, J = 1.7 Hz), 8.95-9.05 (1H, m), 13.55 (1H, brs.) |
TABLE 5
| Ex No. | Strc | $^1$H-NMR δ ppm (DMSO-d6) |
|---|---|---|
| 8 |  | 2.60 (3H, s), 2.72 (3H, s), 7.64 (1H, dd, J = 8.3 Hz, 1.3 Hz), 7.91 (1H, s), 8.20 (1H, d, J = 8.3 Hz), 8.59 (1H, d, J = 1.7 Hz), 8.85-8.95 (1H, m), 13.50 (1H, brs.) |

TABLE 5-continued

| Ex No. | Strc | ¹H-NMR δ ppm (DMSO-d6) |
|---|---|---|
| 9 | 6-methylnaphthalene-1-carbonitrile-3-yl linked to 4-methylthiazole-5-carboxylic acid | 2.54 (3H, s), 2.71 (3H, s), 7.72 (1H, dd, J = 8.6 Hz, 1.2 Hz), 7.95-8.10 (2H, m), 8.54 (1H, d, J = 1.8 Hz), 8.75-8.85 (1H, m) |
| 10 | 6-chloronaphthalene-1-carbonitrile-3-yl linked to 4-methylthiazole-5-carboxylic acid | 2.73 (3H, s), 7.85 (1H, m), 8.08 (1H, s), 8.37 (1H, d, J = 8.8 Hz), 8.70-8.75 (1H, m), 9.02 (1H, s), 13.59 (1H, brs.) |

TABLE 6

| Ex No. | Strc. | ¹H-NMR δ ppm (DMSO-d6) |
|---|---|---|
| 11 | 5,7-dimethylnaphthalene-1-carbonitrile-3-yl linked to 4-methylthiazole-5-carboxylic acid | 2.54 (3H, s), 2.72 (3H, s), 2.76 (3H, s), 7.50 (1H, s), 7.77 (1H, s), 8.55-8.65 (1H, m), 8.75-8.85 (1H, m), 13.52 (1H, brs.) |
| 12 | 7-fluoronaphthalene-1-carbonitrile-3-yl linked to 4-methylthiazole-5-carboxylic acid | 2.73 (3H, s), 7.65-7.90 (1H, m), 8.05-8.35 (2H, m), 8.55-8.80 (1H, m), 8.85-9.10 (1H, m), 13.6 (1H, brs.) |
| 13 | 8-fluoronaphthalene-1-carbonitrile-3-yl linked to 4-methylthiazole-5-carboxylic acid | 2.74 (3H, s), 7.60-7.75 (1H, m), 7.80-8.10 (2H, m), 8.70-8.85 (1H, m), 8.90 (1H, s), 13.60 (1H, brs.) |
| 14 | 8-fluoro-7-methoxynaphthalene-1-carbonitrile-3-yl linked to 4-methylthiazole-5-carboxylic acid | 2.72 (3H, s), 4.05 (3H, s), 7.85-8.00 (2H, m), 8.50-8.60 (1H, m), 8.70-8.80 (1H, m), 13.57 (1H, brs) |
| 15 | 5-fluoro-8-methylnaphthalene-1-carbonitrile-3-yl linked to 4-methylthiazole-5-carboxylic acid | 2.72 (3H, s), 2.96 (3H, s), 7.45-7.55 (1H, m), 7.60-7.65 (1H, m), 8.65 (1H, d, J = 1.9 Hz), 8.82 (1H, d, J = 1.9 Hz), 13.58 (1H, brs) |
| 16 | 5-methylnaphthalene-1-carbonitrile-3-yl linked to 4-methylthiazole-5-carboxylic acid | 2.72 (3H, s), 2.77 (3H, s), 7.60-7.65 (1H, m), 7.70-7.80 (1H, m), 7.90-8.00 (1H, m), 8.55-8.65 (1H, m), 8.75-8.85 (1H, m), 13.55 (1H, brs) |
| 17 | 5-fluoro-6-methylnaphthalene-1-carbonitrile-3-yl linked to 4-methylthiazole-5-carboxylic acid | 2.73 (3H, s), 7.75-7.85 (1H, m), 7.85-7.95 (1H, m), 8.65-8.70 (1H, m), 8.80-8.85 (1H, m), 13.58 (1H, brs.) |

TABLE 6-continued

| Ex No. | Strc. | ¹H-NMR δ ppm (DMSO-d6) |
|---|---|---|
| 18 | (structure: 5,7-difluoro-4-cyano-naphthalen-2-yl thiazole-5-carboxylic acid, 4-methyl) | 2.72 (3H, s), 7.75-7.90 (1H, m), 7.95-8.10 (1H, m), 8.60-8.65 (1H, m), 8.95-9.00 (1H, m), 13.62 (1H, brs) |

TABLE 7

| Ex No. | Strc. | ¹H-NMR δ ppm (DMSO-d6) |
|---|---|---|
| 19 | (structure: 6,8-difluoro-4-cyano-naphthalen-2-yl thiazole-5-carboxylic acid, 4-methyl) | 2.72 (3H, s), 7.65-7.75 (1H, m), 7.80-7.95 (1H, m), 8.75-8.90 (2H, m), 13.58 (1H, brs) |
| 20 | (structure: 5-methoxy-8-fluoro-4-cyano-naphthalen-2-yl thiazole-5-carboxylic acid, 4-methyl) | 2.73 (3H, s), 4.02 (3H, s), 7.20-7.30 (1H, m), 7.50-7.60 (1H, m), 8.60 (1H, d, J = 1.8 Hz), 8.77 (1H, d, J = 1.8 Hz), 13.59 (1H, brs.) |
| 21 | (structure: 5,6,8-trifluoro-4-cyano-naphthalen-2-yl thiazole-5-carboxylic acid, 4-methyl) | 2.73 (3H, s), 8.05-8.20 (1H, m), 8.70-8.80 (1H, m), 8.80-8.90 (1H, m), 13.65 (1H, brs) |

TABLE 7-continued

| Ex No. | Strc. | ¹H-NMR δ ppm (DMSO-d6) |
|---|---|---|
| 22 | (structure: 8-fluoro-4-cyano-naphthalen-2-yl thiazole-5-carboxylic acid, 4-methyl) | 2.73 (3H, s), 7.60-7.70 (1H, m), 7.70-7.80 (1H, m), 8.10-8.20 (1H, m), 8.66 (1H, s), 9.01 (1H, s), 13.59 (1H, brs.) |
| 23 | (structure: 7-fluoro-4-cyano-naphthalen-2-yl thiazole-5-carboxylic acid, 4-methyl) | 2.73 (3H, s), 7.70-7.85 (2H, m), 8.40-8.50 (1H, m), 8.70-8.75 (1H, m), 9.00-9.10 (1H, m), 13.56 (1H, brs) |
| 24 | (structure: 6-fluoro-7-methoxy-4-cyano-naphthalen-2-yl thiazole-5-carboxylic acid, 4-methyl) | 2.72 (3H, s), 4.02 (3H, s), 7.81 (1H, d, J = 11.5 Hz), 8.02 (1H, d, J = 8.5 Hz), 8.50-8.55 (1H, m), 8.85-8.95 (1H, m), 13.54 (1H, brs) |
| 25 | (structure: 7-fluoro-6-methoxy-4-cyano-naphthalen-2-yl thiazole-5-carboxylic acid, 4-methyl) | 2.71 (3H, s), 4.10 (3H, s), 7.45-7.55 (1H, m), 8.15-8.20 (1H, m), 8.55-8.60 (1H, m), 8.80-8.90 (1H, m), 13.53 (1H, brs.) |
| 26 | (structure: 7-fluoro-8-methyl-4-cyano-naphthalen-2-yl thiazole-5-carboxylic acid, 4-methyl) | 2.72 (3H, s), 3.02 (3H, s), 7.55-7.65 (1H, m), 7.90-8.00 (1H, m), 8.50-8.55 (1H, m), 8.85-8.90 (1H, m), 13.55 (1H, brs) |

TABLE 8
| Ex No. | Strc. | ¹H-NMR δ ppm (DMSO-d6) |
|---|---|---|
| 27 | 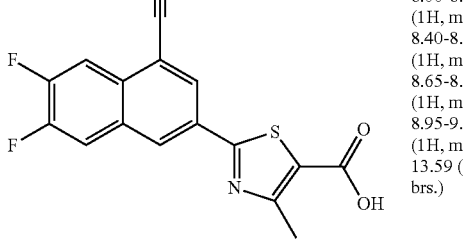 | 2.72 (3H, s), 8.00-8.10 (1H, m), 8.40-8.50 (1H, m), 8.65-8.75 (1H, m), 8.95-9.00 (1H, m), 13.59 (1H, brs.) |
| 28 | | 2.72 (3H, s), 3.94 (3H, s), 7.50-7.55 (1H, m), 7.75-7.80 (1H, m), 8.00-8.10 (1H, m), 8.45-8.50 (1H, m), 8.85-8.90 (1H, m), 13.55 (1H, brs.) |
| 29 | | 2.52 (3H, s), 2.72 (3H, s), 7.50-7.60 (1H, m), 7.91 (1H, s), 8.50-8.60 (1H, m), 8.80-8.90 (1H, m), 13.58 (1H, brs) |
| 30 | | 2.69 (3H, s), 7.85-7.95 (1H, m), 8.15-8.25 (1H, m), 8.60-8.65 (1H, m), 8.90-8.95 (1H, m), 13.57 (1H, brs.) |
| 31 | | 7.70-8.00 (2H, m), 8.05-8.45 (2H, m), 8.52 (1H, s), 8.60-8.85 (1H, m), 8.90-9.15 (1H, m), 13.50-14.00 (1H, m). |
TABLE 8-continued
| Ex No. | Strc. | ¹H-NMR δ ppm (DMSO-d6) |
|---|---|---|
| 32 | 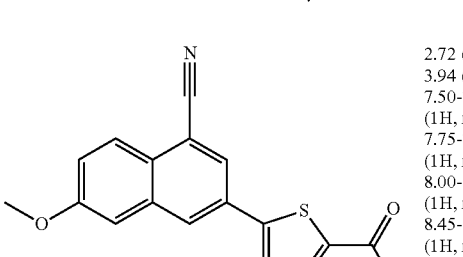 | 7.60-8.15 (3H, m), 8.40-8.60 (1H, m), 8.75-9.05 (2H, m), 13.58 (1H, brs) |
| 33 | | 4.06 (3H, s), 7.90-8.05 (2H, m), 8.53 (1H, s), 8.63 (1H, d, J = 1.8 Hz), 8.80-8.85 (1H, m), 13.79 (1H, brs) |
| 34 | | 2.97 (3H, s), 7.45-7.70 (2H, m), 8.52 (1H, s), 8.72 (1H, d, J = 1.9 Hz), 8.89 (1H, d, J = 1.9 Hz), 13.80 (1H, brs) |
TABLE 9
| Ex No. | Strc. | ¹H-NMR δ ppm (DMSO-d6) |
|---|---|---|
| 35 | 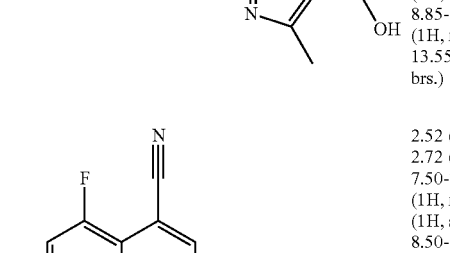 | 7.75-7.85 (1H, m), 7.85-7.95 (1H, m), 8.52 (1H, s), 8.70-8.75 (1H, m), 8.80-8.90 (1H, m), 13.80 (1H, brs.) |
| 36 | | 7.80-7.95 (1H, m), 8.00-8.10 (1H, m), 8.55 (1H, s), 8.65-8.75 (1H, m), 9.00-9.10 (1H, m), 13.84 (1H, brs) |

TABLE 9-continued

| Ex No. | Strc. | ¹H-NMR δ ppm (DMSO-d6) |
|---|---|---|
| 37 | | 7.70-7.80 (1H, m), 7.80-7.95 (1H, m), 8.52 (1H, s), 8.85-8.95 (2H, m), 13.83 (1H, brs) |
| 38 | | 4.02 (3H, s), 7.20-7.30 (1H, m), 7.50-7.60 (1H, m), 8.53 (1H, s), 8.65 (1H, d, J = 1.7 Hz), 8.82 (1H, d, J = 1.7 Hz), 13.81 (1H, brs.) |
| 39 | | 8.05-8.20 (1H, m), 8.56 (1H, s), 8.75-8.85 (1H, m), 8.90-8.95 (1H, m), 13.87 (1H, brs) |
| 40 | | 7.60-7.85 (2H, m), 8.16 (1H, d, J = 8.2 Hz), 8.53 (1H, s), 8.71 (1H, s), 9.07 (1H, s), 13.80 (1H, brs.) |
| 41 | | 4.09 (3H, s), 7.40-7.50 (1H, m), 8.05-8.15 (1H, m), 8.45 (1H, s), 8.55-8.60 (1H, m), 8.80-8.85 (1H, m), 13.73 (1H, brs.) |

TABLE 9-continued

| Ex No. | Strc. | ¹H-NMR δ ppm (DMSO-d6) |
|---|---|---|
| 42 | | 3.04 (3H, s), 7.60-7.70 (1H, m), 7.95-8.05 (1H, m), 8.53 (1H, s), 8.60 (1H, d, J = 2.0 Hz), 8.97 (1H, d, J = 2.0 Hz), 13.78 (1H, brs) |

TABLE 10

| Ex No. | Strc. | (solv.) ¹H-NMR δ ppm |
|---|---|---|
| 43 | | (DMSO-d6) 2.54 (3H, s), 7.50-7.65 (1H, m), 7.94 (1H, s), 8.53 (1H, s), 8.60-8.65 (1H, m), 8.90-9.00 (1H, m), 13.82 (1H, brs) |
| 44 | | (CDCl3) 7.70-7.95 (2H, m), 7.95-8.10 (2H, m), 8.25-8.35 (1H, m), 8.46 (1H, s). |
| 45 | | (DMSO-d6) 7.70-8.00 (2H, m), 8.10-8.45 (2H, m), 8.75-8.85 (1H, m), 9.15 (1H, s). |
| 46 | | (DMSO-d6) 7.70-7.95 (2H, m), 8.05-8.30 (2H, m), 8.70 (1H, s), 8.80-8.90 (1H, m), 9.10 (1H, s). |

TABLE 10-continued

| Ex No. | Strc. | (solv.) $^1$H-NMR δ ppm |
|---|---|---|
| 47 | [structure: naphthalene with CN, connected to oxazole with methyl and COOH] | (DMF-d7) 2.75 (3H, s), 7.95-8.30 (2H, m), 8.35-8.70 (2H, m), 8.75-8.85 (1H, m), 9.25 (1H, s). |
| 48 | [structure: naphthalene with CN, OH, F substituents, connected to thiazole with methyl and COOH] | (DMSO-d6) 2.73 (3H, s), 7.55-7.65 (1H, m), 7.86 (1H, d, 9.1 Hz), 8.49 (1H, d, J = 1.6 Hz), 8.70-8.75 (1H, m), 10.88 (1H, s), 13.56 (1H, brs) |
| 49 | [structure: naphthalene with CN, OH substituents, connected to thiazole with methyl and COOH] | (DMSO-d6) 2.72 (3H, s), 7.40-7.55 (2H, m), 7.95-8.05 (1H, m), 8.35-8.40 (1H, m), 8.70-8.80 (1H, m), 10.48 (1H, s), 13.53 (1H, brs.) |

Test Example 1

Xanthine Oxidase Inhibitory Activity (1) Preparation of Test Compounds

Test compounds were dissolved in DMSO (Wako) at 40 mM concentration and then diluted to intended concentrations with phosphate-buffered saline (PBS).

(2) Method for Measurement

Xanthine oxidase (from bovine milk, Sigma) was prepared with phosphate-buffered saline (PBS) at 0.02 units/mL, and then the solution was added to 96 well plates at 50 μL/well. In addition, test compounds diluted with PBS were added at 50 μL/well. Xanthine (Wako) at 200 μM prepared with PBS was added at 100 μL/well, and the reaction was measured for 10 minutes at room temperature. Absorbance at 290 nm was measured using a microplate reader SpectraMax Plus 384 (Molecular device). The absorbance under a condition without xanthine is 0%, and control without test compounds is 100%. Fifty % inhibitory concentration ($IC_{50}$) of test compounds was calculated (Table 11). Ex. No. in the table indicates example number.

TABLE 11

| Ex. No. | 1 | 2 | 3 | 4 | 5 | 6 | 7 | 8 | 9 |
|---|---|---|---|---|---|---|---|---|---|
| $IC_{50}$(nM) | 11 | 13 | 38 | 20 | 81 | 8 | 7 | 11 | 26 |

| Ex. No. | 12 | 13 | 15 | 22 | 31 |
|---|---|---|---|---|---|
| $IC_{50}$(nM) | 4 | 8 | 7 | 7 | 2 |

Test Example 2

Inhibitory Activity of Uric Acid Transport with Human URAT1 Expressing Cells (1) Preparation of Transiently Human URAT1 Expressing Cells Full length human URAT1 cDNA (NCBI Accession No. NM_144585) was subcloned into expression vector, pcDNA3.1 (Invitrogen). Human URAT1 expression vector was transfected into COS7 cells (RIKEN CELL BANK RCB0539) using Lipofectamine 2000 (Invitrogen). COS7 cells were seeded in collagen-coated 24 well plates (Japan Becton Dickinson) at 90-95% confluency and cultured in D-MEM culture medium (Invitrogen) containing 10% fetal bovine serum (Sanko Junyaku) for 2 hours at 37° C. under the condition of 5% $CO_2$. For 1 well, 2 μL of Lipofectamine 2000 was diluted in 50 μL of OPTI-MEM (Invitrogen) and allowed to stand at room temperature for 7 minutes (hereinafter referred to as Lipo2000-OPTI). For 1 well, 0.8 μg of human URAT1 expression vector was diluted in 50 μL of OPTI-MEM (Invitrogen) and combined gently with Lipo2000-OPTI. After standing at room temperature for 25 minutes, the mixture was added to COS7 cells at 100 μL/well. Furthermore, COS7 cells were cultured for 2 days at 37° C. under the condition of 5% $CO_2$ and used for measuring inhibitory activity on the uptake.

(2) Preparation of Test Compounds

Test compounds were dissolved in DMSO (Wako) at 10 mM concentration and then diluted to 2 times higher concentration than intended with pre-treatment buffer (125 mM sodium gluconate, 4.8 mM potassium gluconate, 1.2 mM potassium dihydrogen phosphate, 1.2 mM magnesium sulfate, 1.3 mM calcium gluconate, 5.6 mM glucose, 25 mM Hepes, pH 7.4). Pre-treatment buffer without test compounds was used for control. In addition, an equal volume of pre-treatment buffer containing $^{14}$C-labeled uric acid (American Radiolabeled Chemicals, Inc.) was added to test compounds and control, and finally assay buffer including 20 μM uric acid was prepared.

(3) Method for Measurement

All tests were performed on hot-plate at 37° C. Pre-treatment buffer and assay buffer were incubated at 37° C. and then used for assays. Medium was removed from plates, and 700 μL of pre-treatment buffer was added, and the cells were pre-incubated for 10 minutes. After repeating same step, pre-treatment buffer was removed, and assay buffer was added at 400 μL/well. The uptake reaction was carried out for 5 minutes. After terminating the reaction, assay buffer was rapidly removed, and the cells were washed twice with addition of ice-cold pre-treatment buffer at 1.2 mL/well. Then, the cells were lysed by addition of 0.2N sodium hydroxide at 300 μL/well. The lysed solutions were transferred into Picoplate (PerkinElmer), and Microscinti 40 (PerkinElmer) was added at 600 μL/well. After mixing, the radioactivity was counted in a liquid scintillation counter (PerkinElmer). The radioactivity in COS7 cells not transfected with URAT1 expression vector was also counted under the same condition as control. In addition, percent inhibition of test compounds was calculated according to the formula described below. As a result, it was shown that all Examples 2, 6, 7, 12, 13, 15, 22 and 31 have over 80% inhibition in a concentration of 100 μM.

Percent inhibition (%)=[1−(B−C)/(A−C)]×100

A: Radioactivity in control
B: Radioactivity in the case of addition of test compounds
C: Radioactivity in COST cells not transfected with URAT1 expression vector

INDUSTRIAL APPLICABILITY

The fused ring derivatives represented by the formula (I) of the present invention or prodrugs thereof, or pharmaceutically acceptable salts thereof exert an excellent xanthine oxidase inhibitory activity, and therefore, can exert an inhibitory activity of uric acid production and lower the blood uric acid level. Therefore, the present invention can provide an agent for the prevention or treatment of hyperuricemia, gouty tophus, gouty arthritis, renal disorder associated with hyperuricemia, urinary calculi or the like.

The invention claimed is:
1. A fused ring derivative represented by the formula:

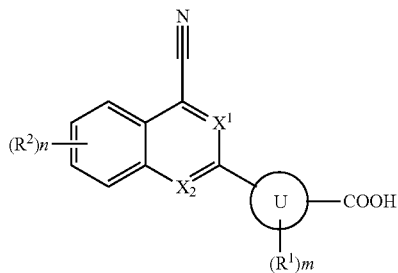

wherein
$X^1$ and $X^2$ independently represent CH or N;
ring U represents $C_6$ aryl or 5 or 6-membered heteroaryl;
m represents an integral number from 0 to 2;
n represents an integral number from 0 to 3;
$R^1$ represents a hydroxy group, a halogen atom, amino or $C_{1-6}$ alkyl, and when m is 2, two $R^1$ are optionally different from each other;
$R^2$ represents any of (1) to (11):
  (1) a halogen atom;
  (2) a hydroxy group;
  (3) cyano;
  (4) nitro;
  (5) carboxy;
  (6) carbamoyl;
  (7) amino;
  (8) $C_{1-6}$ alkyl, $C_{2-6}$ alkenyl or $C_{1-6}$ alkoxy each of which may independently have any group selected from substituent group α;
  (9) $C_{2-6}$ alkynyl, $C_{1-6}$ alkylsulfonyl, mono(di)$C_{1-6}$ alkylsulfamoyl, $C_{2-7}$ acyl, $C_{1-6}$ alkoxycarbonyl, $C_{1-6}$ alkoxycarbonyloxy, mono(di)$C_{1-6}$ alkylamino, mono(di)$C_{1-6}$ alkoxy $C_{1-6}$ alkylamino, $C_{1-6}$ alkoxy $C_{1-6}$ alkyl($C_{1-6}$ alkyl)amino, $C_{2-7}$ acylamino, $C_{1-6}$ alkoxycarbonylamino, $C_{1-6}$ alkoxycarbonyl($C_{1-6}$ alkyl) amino, mono(di)$C_{1-6}$ alkylcarbamoyl, mono(di)$C_{1-6}$ alkoxy $C_{1-6}$ alkylcarbamoyl, $C_{1-6}$ alkoxy $C_{1-6}$ alkyl ($C_{1-6}$ alkyl)carbamoyl, mono(di)$C_{1-6}$ alkylaminocarbonylamino, $C_{1-6}$ alkylsulfonylamino or $C_{1-6}$ alkylthio;
  (10) $C_{3-8}$ cycloalkyl, 3 to 8-membered heterocycloalkyl, $C_{5-8}$ cycloalkenyl or 5 to 8-membered heterocycloalkenyl;
  (11) $C_6$ aryl, $C_6$ aryloxy, $C_6$ arylcarbonyl, 5 or 6-membered heteroaryl, 5 or 6-membered heteroaryloxy, 5 or 6-membered heteroarylcarbonyl, $C_6$ arylamino, $C_6$ aryl($C_{1-6}$ alkyl)amino, 5 or 6-membered heteroarylamino or 5 or 6-membered heteroaryl($C_{1-6}$ alkyl) amino; and when n is 2 or 3, these $R^2$ are optionally different from each other, and when two $R^2$ bound to the neighboring atoms exist and independently represent $C_{1-6}$ alkyl or $C_{1-6}$ alkoxy each of which may have $C_{1-6}$ alkoxy, these two $R^2$ optionally form a 5 to 8-membered ring together with the binding atoms;
substituent group α consists of a fluorine atom, a hydroxy group, amino, carboxy, $C_{1-6}$ alkoxy, mono(di)$C_{1-6}$ alkylamino, mono(di)$C_{1-6}$ alkoxy $C_{1-6}$ alkylamino, $C_{1-6}$ alkoxy $C_{1-6}$ alkyl($C_{1-6}$ alkyl)amino, $C_{1-6}$ alkoxycarbonylamino, $C_{2-7}$ acyl, $C_{1-6}$ alkoxycarbonyl, mono(di)$C_{1-6}$ alkylcarbamoyl, mono(di)$C_{1-6}$ alkoxy $C_{1-6}$ alkylcarbamoyl, $C_{1-6}$ alkoxy $C_{1-6}$ alkyl($C_{1-6}$ alkyl)carbamoyl, $C_{1-6}$ alkylsulfonylamino, $C_{2-7}$ acylamino, $C_{1-6}$ alkoxycarbonylamino, $C_{3-8}$ cycloalkyl, 3 to 8-membered heterocycloalkyl, $C_6$ aryl and 5 or 6-membered heteroaryl, or a pharmaceutically acceptable salt thereof.

2. A fused ring derivative as claimed in claim 1, wherein $X^1$ represents CH, or a pharmaceutically acceptable salt thereof.

3. A fused ring derivative as claimed in claim 1, wherein $X^2$ represents CH, or a pharmaceutically acceptable salt thereof.

4. A fused ring derivative as claimed in claim 1, wherein ring U represents a benzene ring, a pyridine ring, a thiazole ring, a pyrazole ring or a thiophene ring, or a pharmaceutically acceptable salt thereof.

5. A fused ring derivative as claimed in claim 4, wherein m is 0, or m is 1 and ring U is any one of rings represented by the following formulae:

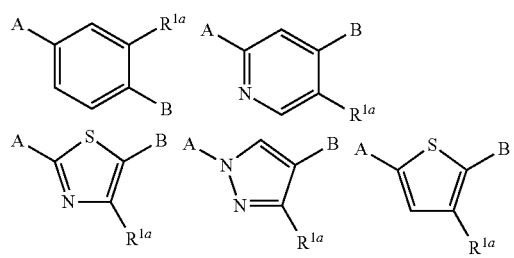

in the formulae, $R^{1a}$ represents a hydroxy group, amino or $C_{1-6}$ alkyl; A represents a bond with the fused ring; and B represents a bond with carboxy; respectively, or a pharmaceutically acceptable salt thereof.

6. A fused ring derivative as claimed in claim 5, wherein m is 0, or m is 1 and ring U is a thiazole ring represented by the formula:

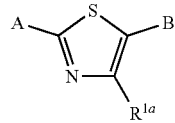

or a pharmaceutically acceptable salt thereof.

7. A fused ring derivative as claimed in claim 5, wherein m is 0, or m is 1 and ring U is a pyridine ring represented by the formula:

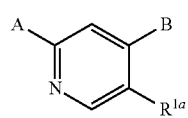

or a pharmaceutically acceptable salt thereof.

8. A fused ring derivative as claimed in claim 6, wherein m is 1 and $R^{1a}$ represents a methyl group; n is 0, or n is 1 to 3 and $R^2$ represents a halogen atom, a hydroxy group or $C_{1-6}$ alkyl which may have 1 to 3 fluorine atoms, or a pharmaceutically acceptable salt thereof.

9. A fused ring derivative as claimed in claim 7, wherein m is 0, or m is 1 and $R^{1a}$ represents a hydroxy group and $R^2$ represents a halogen atom, a hydroxy group or $C_{1-6}$ alkyl which may have 1 to 3 fluorine atoms, or a pharmaceutically acceptable salt thereof.

10. A fused ring derivative as claimed in claim 1, wherein n is 0, or n is 1 to 3 and $R^2$ represents a halogen atom, a hydroxy group, or $C_{1-6}$ alkyl or $C_{1-6}$ alkoxy each of which may independently have any 1 to 3 groups selected from a fluorine atom, a hydroxy group and amino, or a pharmaceutically acceptable salt thereof.

11. A fused ring derivative as claimed in claim 10, wherein n is 0, or n is 1 to 3 and $R^2$ represents a halogen atom, or $C_{1-6}$ alkyl or $C_{1-6}$ alkoxy each of which may independently have any 1 to 3 groups selected from a fluorine atom, a hydroxy group and amino; and ring U represents a thiazole ring or a pyridine ring, or a pharmaceutically acceptable salt thereof.

12. A fused ring derivative as claimed in claim 1, wherein m is 0, or a pharmaceutically acceptable salt thereof.

13. A fused ring derivative as claimed in claim 1, wherein n is 0, or a pharmaceutically acceptable salt thereof.

14. A fused ring derivative as claimed in claim 10, wherein n is 1 to 3 and $R^2$ represents a fluorine atom, or a pharmaceutically acceptable salt thereof.

15. A fused ring derivative as claimed in claim 11, represented by the formula:

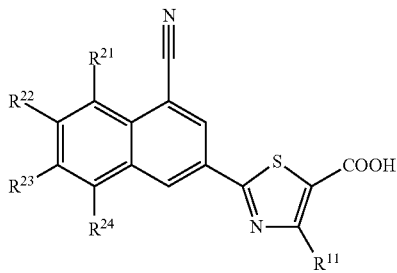

wherein $R^{21}$ represents a hydrogen atom, a fluorine atom or a methyl group; $R^{22}$ represents a hydrogen atom or a fluorine atom; $R^{23}$ represents a hydrogen atom, a fluorine atom or a methyl group; $R^{24}$ represents a hydrogen atom or a fluorine atom; and $R^{11}$ represents a hydrogen atom or a methyl group, or a pharmaceutically acceptable salt thereof.

16. A fused ring derivative as claimed in claim 1, which is a xanthine oxidase inhibitor, or a pharmaceutically acceptable salt thereof.

17. A pharmaceutical composition comprising as an active ingredient a fused ring derivative as claimed in claim 1, or a pharmaceutically acceptable salt thereof.

18. A pharmaceutical composition as claimed in claim 17, which is an agent for the treatment of a disease selected from the group consisting of hyperuricemia, gouty tophus, gouty arthritis, renal disorder associated with hyperuricemia and urinary calculi.

19. A pharmaceutical composition as claimed in claim 18, which is an agent for treatment of hyperuricemia.

20. A pharmaceutical composition as claimed in claim 17, which is an agent for lowering plasma uric acid level.

21. A pharmaceutical composition as claimed in claim 17, which is a uric acid production inhibitor.

22. A fused ring derivative as claimed in claim 2, wherein $X^2$ represents CH, or a pharmaceutically acceptable salt thereof.

23. A method for the treatment of a disease selected from the group consisting of hyperuricemia, gouty tophus, gouty arthritis, renal disorder associated with hyperuricemia and urinary calculi, which comprises administering to a patient in need thereof an effective amount of a fused ring derivative as claimed in claim 1 or a pharmaceutically acceptable salt thereof.

24. The method as claimed in claim 23, which is for the treatment of hyperuricemia.

25. A method for lowering serum uric acid level, which comprises administering to a patient in need thereof an effective amount of a fused ring derivative as claimed in claim 1 or a pharmaceutically acceptable salt thereof.

26. A method for the inhibition of uric acid production, which comprises administering to a patient in need thereof an effective amount of a fused ring derivative as claimed in claim 1 or a pharmaceutically acceptable salt thereof.

27. A fused ring derivative represented by the formula:

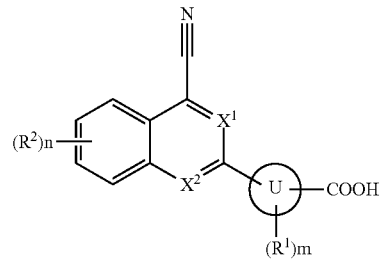

wherein
$X^1$ and $X^2$ independently represent CH or N;
ring U represents $C_6$ aryl or 5 or 6-membered heteroaryl;
m represents an integral number from 0 to 2;
n represents an integral number from 0 to 3;
$R^1$ represents a hydroxy group, a halogen atom, amino or $C_{1-6}$ alkyl, and when m is 2, two $R^1$ are optionally different from each other;
$R^2$ represents any of (1) to (11):
(1) a halogen atom;
(2) a hydroxy group;
(3) cyano;
(4) nitro;
(5) carboxy;
(6) carbamoyl;
(7) amino;
(8) $C_{1-6}$ alkyl, $C_{2-6}$ alkenyl or $C_{1-6}$ alkoxy each of which may independently have any group selected from substituent group a;
(9) $C_{2-6}$ alkynyl, $C_{1-6}$ alkylsulfonyl, mono(di)$C_{1-6}$ alkylsulfamoyl, $C_{2-7}$ acyl, $C_{1-6}$ alkoxycarbonyl, $C_{1-6}$ alkoxycarbonyloxy, mono(di)$C_{1-6}$ alkylamino, mono(di)$C_{1-6}$ alkoxy $C_{1-6}$ alkylamino, $C_{1-6}$ alkoxy $C_{1-6}$ alkyl($C_{1-6}$ alkyl)amino, $C_{2-7}$ acylamino, $C_{1-6}$ alkoxycarbonylamino, $C_{1-6}$ alkoxycarbonyl($C_{1-6}$ alkyl)amino, mono(di)$C_{1-6}$ alkylcarbamoyl, mono(di)$C_{1-6}$ alkoxy $C_{1-6}$ alkylcarbamoyl, $C_{1-6}$ alkoxy $C_{1-6}$ alkyl($C_{1-6}$ alkyl)carbamoyl, mono(di)$C_{1-6}$ alkylaminocarbonylamino, $C_{1-6}$ alkylsulfonylamino or $C_{1-6}$ alkylthio;

(10) $C_{3-8}$ cycloalkyl, 3 to 8-membered heterocycloalkyl, $C_{5-8}$ cycloalkenyl or 5 to 8-membered heterocycloalkenyl;

(11) $C_6$ aryl, $C_6$ aryloxy, $C_6$ arylcarbonyl, 5 or 6-membered heteroaryl, 5 or 6-membered heteroaryloxy, 5 or 6-membered heteroarylcarbonyl, $C_6$ arylamino, $C_6$ aryl($C_{1-6}$ alkyl)amino, 5 or 6-membered heteroarylamino or 5 or 6-membered heteroaryl($C_{1-6}$ alkyl) amino; and when n is 2 or 3, these $R^2$ are optionally different from each other, and when two $R^2$ bound to the neighboring atoms exist and independently represent $C_{1-6}$ alkyl or $C_{1-6}$ alkoxy each of which may have $C_{1-6}$ alkoxy, these two $R^2$ optionally form a 5 to 8-membered ring together with the binding atoms;

substituent group a consists of a fluorine atom, a hydroxy group, amino, carboxy, $C_{1-6}$ alkoxy, mono(di)$C_{1-6}$ alkylamino, mono(di)$C_{1-6}$ alkoxy alkylamino, $C_{1-6}$ alkoxy $C_{1-6}$ alkyl($C_{1-6}$ alkyl)amino, $C_{1-6}$ alkoxycarbonylamino, $C_{2-7}$ acyl, $C_{1-6}$ alkoxycarbonyl, mono(di)$C_{1-6}$ alkylcarbamoyl, mono(di)$C_{1-6}$ alkoxy $C_{1-6}$ alkylcarbamoyl, $C_{1-6}$ alkoxy $C_{1-6}$ alkyl($C_{1-6}$ alkyl)carbamoyl, $C_{1-6}$ alkylsulfonylamino, $C_{2-7}$ acylamino, $C_{1-6}$ alkoxycarbonylamino, $C_{3-8}$ cycloalkyl, 3 to 8-membered heterocycloalkyl, $C_6$ aryl and 5 or 6-membered heteroaryl, and wherein the formula contains one or more groups selected from the group consisting of a hydroxy group and an amino group substituted by:

$C_{1-6}$ alkyl-CO—;

$C_6$ aryl-CO—;

$C_{1-6}$ alkyl-O—$C_{1-6}$ alkylene-CO—;

$C_{1-6}$ alkyl-OCO—$C_{1-6}$ alkylene-CO—;

$C_{1-6}$ alkyl-OCO—;

$C_{1-6}$ alkyl-O—$C_{1-6}$ alkylene-OCO—;

$C_{1-6}$ alkyl-COO—$C_{1-6}$ alkylene;

$C_{1-6}$ alkyl-OCOO—$C_{1-6}$;

$C_{3-8}$ cycloalkyl-OCOO—$C_{1-6}$ alkylene;

and a carboxy group substituted by $C_{1-6}$ alkyl;

$C_{1-6}$ alkyl-COO—$C_{1-6}$ alkylene;

$C_{1-6}$ alkyl-OCOO—$C_{1-6}$ alkylene; and $C_{3-8}$ cycloalkyl-OCOO—$C_{1-6}$ alkylene, or a pharmaceutically acceptable salt thereof.

* * * * *